United States Patent [19]

Pallos et al.

[11] 4,415,353

[45] * Nov. 15, 1983

[54] HERBICIDE COMPOSITIONS

[75] Inventors: Ferenc M. Pallos, Walnut Creek; Mervin E. Brokke, Moraga; Duane R. Arneklev, Sunnyvale, all of Calif.

[73] Assignee: Stauffer Chemical Company, Westport, Conn.

[*] Notice: The portion of the term of this patent subsequent to May 3, 1994 has been disclaimed.

[21] Appl. No.: 441,963

[22] Filed: Nov. 15, 1982

Related U.S. Application Data

[60] Division of Ser. No. 369,322, Apr. 16, 1982, which is a division of Ser. No. 196,518, Oct. 14, 1980, abandoned, which is a division of Ser. No. 930,967, Aug. 4, 1978, Pat. No. 4,269,618, which is a division of Ser. No. 208,041, Dec. 9, 1971, Pat. No. 4,137,070, which is a continuation-in-part of Ser. No. 134,868, Apr. 16, 1971, abandoned.

[51] Int. Cl.$^3$ ................... A01N 37/00; A01N 37/18
[52] U.S. Cl. ............................. 71/100; 71/118
[58] Field of Search ................... 71/118, 100

[56] References Cited

U.S. PATENT DOCUMENTS

| | | | |
|---|---|---|---|
| 2,864,684 | 12/1958 | Speziale | 71/2.7 |
| 3,131,509 | 5/1964 | Hoffmann | 71/77 |
| 3,133,810 | 5/1964 | Hamm | 71/101 |
| 3,661,991 | 5/1972 | NcNulty et al. | 260/558 D |
| 3,677,739 | 7/1972 | Horrom et al. | 71/118 |
| 3,719,466 | 3/1973 | Ahle | 71/88 |
| 3,794,683 | 2/1974 | Gassner et al. | 260/562 B |
| 3,839,466 | 10/1974 | Teach | 260/562 A |
| 4,033,756 | 7/1977 | Hoffmann | 71/90 |
| 4,208,203 | 6/1980 | Hoffmann | 71/95 |

OTHER PUBLICATIONS

Hamm et al. I, "Effect of Variations etc.;" (1957), J. of Ag. & Food Chem. 5, pp. 30–32.
Hamm et al. II, "Relation of Herbicidal, etc.;"(1956), J. Ag. Food Chem. 4, pp. 518–522.
McRae, "Herbicides", (1963), CA 61, p. 1190d, (1964).
Sterling Drug, "Bis (haloalkanoyl) Diamines", (1962), CA 58, pp. 5520–5521, (1963).
Hamm et al., ;37 Herbicides", (1958), CA 54, pp. 20059–20060, (1960).
Berberian, "In Vitro and In Vivo Amebicidan, etc.", (1961), CA 56, p. 6004, (1962).

*Primary Examiner*—Glennon H. Hollrah
*Attorney, Agent, or Firm*—Harry A. Pacini

[57] ABSTRACT

Herbicidal compositions comprising an active thiolcarbamate herbicide and an amide of dichloroacetic acid antidote therefor and the methods of use of such herbicidal compositions are described herein.

8 Claims, No Drawings

HERBICIDE COMPOSITIONS

This is a division of application Ser. No. 369,322, filed Apr. 16, 1982 which in turn is a divisional of U.S. Ser. No. 196,518, filed Oct. 14, 1980, now abandoned, which in turn is a divisional of U.S. Ser. No. 930,967, filed Aug. 4, 1978, now U.S. Pat. No. 4,269,618, which in turn is a divisional of U.S. Ser. No. 208,041, filed Dec. 9, 1971, now U.S. Pat. No. 4,137,070, which in turn is a continuation-in-part of U.S. Ser. No. 134,868, filed Apr. 16, 1971, now abandoned.

BACKGROUND OF THE INVENTION

Among the many herbicidal compounds commercially available the thiolcarbamates alone or admixed with other herbicides, such as the triazines, have reached a relatively high degree of commercial success. These herbicides are immediately toxic to a large number of weed pests at different concentrations varying with the resistance of the weed pests. Some examples of these compounds are described and claimed in the U.S. Pat. Nos. 2,913,327, 3,037,853, 3,175,897, 3,185,720, 3,198,786 and 3,582,314. It has been found in practice that the use of these thiolcarbamates as herbicides on crops sometimes causes serious injuries to the crop plant. When used in the recommended amounts in the soil to control many broadleaf weeds and grasses, serious malformation and stunting of the crop plants result. This abnormal growth in the crop plants results in loss of crop yield. Previous attempts to overcome this problem involves the treatment of the crop seed with certain antagonistic agents prior to planting, see U.S. Pat. No. 3,131,509. These antagonistic agents have not been notably successful.

DESCRIPTION OF THE INVENTION

It has been discovered that plants can be protected against injury by the thiolcarbamates alone or mixed with other compounds and/or the tolerance of the plants can be substantially increased to the active compounds of the above-noted U.S. Patents by adding to the soil an antidote compound corresponding to the following formula:

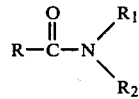

wherein R can be selected from the group consisting of haloalkyl; haloalkenyl; alkyl; alkenyl; cycloalkyl; cycloalkylalkyl; halogen; hydrogen; carboalkoxy; N-alkenylcarbamylalkyl; N-alkenylcarbamyl; N-alkyl-N-alkynylcarbamyl; N-alkyl-N-alkynylcarbamylalkyl; N-alkenylcarbamylalkoxyalkyl; N-alkyl-N-alkynylcarbamylalkoxyalkyl; alkynoxy; haloalkoxy; thiocyanatoalkyl; alkenylaminoalkyl; alkylcarboalkyl; cyanoalkyl; cyanatoalkyl; alkenylaminosulfonoalkyl; alkylthioalkyl; haloalkylcarbonyloxyalkyl; alkyoxycarboalkyl; haloalkenylcarbonyloxyalkyl; hydroxyhaloalkyloxyalkyl; hydroxyalkylcarboalkyoxyalkyl; hydroxyalkyl; alkoxysulfonoalkyl; furyl, thienyl; alkyldithiolenyl; thienalkyl; phenyl and substituted phenyl wherein said substituents can be selected from halogen, alkyl, haloalkyl, alkoxy, carbamyl, nitro, carboxylic acids and their salts, haloalkylcarbamyl; phenylalkyl; phenylhaloalkyl; phenylalkenyl; substituted phenylalkenyl wherein said substituents can be selected from halogen, alkyl, alkoxy, halophenoxy, phenylalkoxy; phenylalkylcarboxyalkyl; pheylcycloalkyl; halophenylalkenoxy; halothiophenylalkyl; halophenoxyalkyl; bicycloalkyl; alkenylcarbamylpyridinyl; alkynylcarbamylpyridinyl; dialkenylcarbamylbicycloalkenyl; alkynylcarbamylbicycloalkenyl; $R_1$ and $R_2$ can be the same or different and can be selected from the group consisting of alkenyl; haloalkenyl; hydrogen; alkyl; haloalkyl; alkynyl; cyanoalkyl; hydroxyalkyl; hydroxyhaloalkyl; haloalkylcarboxyalkyl; alkylcarboxyalkyl; alkoxycarboxyalkyl; thioalkylcarboxyalkyl; alkoxycarboalkyl; alkylcarbamyloxyalkyl; amino; formyl; haloalkyl-N-alkylamido; haloalkylamido; haloalkylamidoalkyl; haloalkyl-N-alkylamidoalkyl; haloalkylamidoalkenyl; alkylimino; cycloalkyl; alkylcycloalkyl; alkoxyalkyl; alkylsulfonyloxyalkyl; mercaptoalkyl; alkylaminoalkyl; alkoxycarboalkenyl; haloalkylcarbonyl; alkylcarbonyl; alkenylcarbamyloxyalkyl; cycloalkylcarbamyloxyalkyl; alkoxycarbonyl; haloalkoxycarbonyl; halophenylcarbamyloxyalkyl; cycloalkenyl; phenyl; substituted phenyl wherein said substituents can be selected from alkyl, halogen, haloalkyl, alkoxy, haloalkylamido, phthalamido, hydroxy, alkylcarbamyloxy, alkenylcarbamyloxy, alkylamido, haloalkylamido, alkylcarboalkenyl; phenylsulfonyl; phenylalkyl; substituted phenylalkyl wherein said substituents can be selected from halogen, alkyl; dioxyalkylene, halophenoxyalkylamidoalkyl; alkylthiodiazolyl; piperidylalkyl; thiazolyl; alkylthiazolyl; benzothiazolyl; halobenzothiazolyl; furylalkyl; pyridyl; alkylpyridyl; alkyloxazolyl; tetrahydrofurylalkyl; 3-cyano, 4,5-polyalkylene-thienyl; α-haloalkylacetamidophenylalkyl; α-haloalkylacetamidonitrophenylalkyl; α-haloalkylacetamidohalophenylalkyl; cyanoalkenyl; $R_1$ and $R_2$ when taken together can form a structure consisting of piperidinyl; alkylpiperidinyl; alkyltetrahydropyridyl; morpholyl; alkylmorpholyl; azobicyclononyl; benzoalkylpyrrolidinyl; oxazolidyl; alkyloxazolidyl; perhydroquinolyl; alkylaminoalkenyl; provided that when $R_1$ is hydrogen $R_2$ is other than hydrogen and halophenyl.

The compounds represented by the above formula can be synthesized by mixing together an appropriate acid chloride with an appropriate amine. A solvent such as benzene can be used if desired. The reaction is preferably carried out at reduced temperatures. After the reaction is complete, the end-product is brought to room temperature and can be readily separated.

In order to illustrate the merits of the present invention, reference is made to the following examples.

EXAMPLE 1

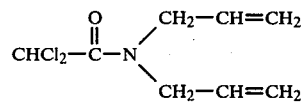

A solution was made by dissolving 3.7 g. (0.025 mole) of dichloroacetyl chloride in 100 ml. of methylene dichloride which was then cooled to about 5° C. in an ice bath. Then, 4.9 g. (0.05 mole) of diallyl amine was added dropwise while the temperature was maintained at below about 10° C. The mixture was then stirred at room temperature for about 4 hours and washed twice with water and dried over magnesium sulfate, filtered and stripped. The yield was 4.0 g., $n_C^{30}$ - 1.4990.

EXAMPLE 2

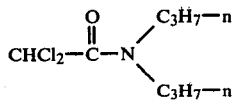

A solution was made by dissolving 3.7 g. (0.025 mole) of dichloroacetyl chloride in 100 ml. of methylene dichloride which was then cooled to about 10° C. in an ice bath. Then, 5.1 g. (0.05 mole) of di-n-propylamine was added dropwise while the temperature was maintained at below about 10° C. The mixture was then stirred at room temperature overnight and washed twice with water and dried over magnesium sulfate, filtered and stripped. The yield was 3.6 g., $n_D^{30}$ - 1.4778.

EXAMPLE 3

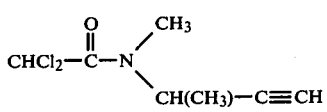

A solution was made by dissolving 3.7 g. (0.025 mole) of dichloroacetyl chloride in 80 ml. of methylene dichloride which was then cooled to about 10° C. in an ice bath. Then, 4.2 g. (0.05 mole) of N-methyl, N-1-methyl-3-propynylamine in 20 ml. of methylene dichloride was added dropwise while the temperature was maintained about 10° C. The mixture was then stirred at room temperature for about 4 hours and washed twice with water and dried over magnesium sulfate, filtered and stripped. The yield was 2.9 g., $n_D^{30}$ - 1.4980.

EXAMPLE 4

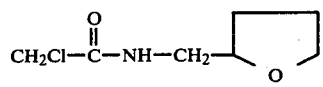

A solution was formed containing 100 ml. acetone, 5.05 g. furfuryl amine (0.1 mole), then stirred with the addition of 7 ml. triethylamine at 15° C. Then, 5.7 g. of monochloro acetyl chloride was added and stirred for 15 more minutes, wherein 500 ml. of water was added. The reaction mass was filtered, washed with dilute hydrochloric acid in additional water, and then dried to constant weight.

EXAMPLE 5

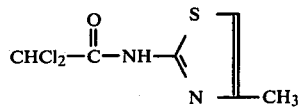

A solution was formed consisting of 5.7 g. (0.05 mole) of amino methyl thiazole in 100 ml. of benzene with 7 ml. of triethylamine. This solution was stirred at 10°–15° C. and then 5.2 ml. (0.05 mole) of dichloro acetyl chloride was added dropwise. The reaction was stirred at room temperature for 10 minutes. Then, 100 ml. water was added and the solution was then washed with benzene solution, dried over magnesium sulfate and then filtered to remove the solvent.

EXAMPLE 6

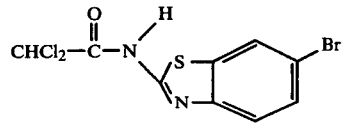

A solution was formed containing 200 ml. acetone and 17.5 g. (0.05 mole) of 2-amino-6-bromo benzothiazole and 7 ml. of triethylamine. The solution was stirred 15° C. with cooling. Then, 5.2 ml. (0.05 mole) of dichloroacetyl chloride was added slowly. This solution was stirred at room temperature for ten minutes. The solid form was filtered off, which solid was washed with ether, then cold water, and then filtered again and dried at 40°–50° C.

EXAMPLE 7

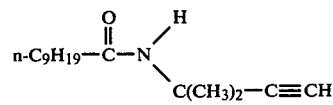

3.4 g. of 3-methyl-3-butynyl amine was dissolved in 50 ml. of methylene chloride, 4.5 g. of triethylamine was added and 7.6 g. of decanoyl chloride was added dropwise with stirring and cooling in a water bath. When the reaction was complete the mixture washed with water, dried and the solvent stripped off to give 7.1 g. of product.

EXAMPLE 8

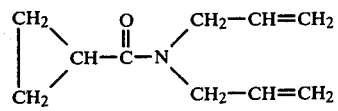

A solution was formed containing 5.9 g. of diallyl amine dissolved in 15 ml. of methylene chloride and 6.5 g. of triethylamine. Then, 6.3 g. of cyclopropane carbonylchloride was added dropwise with stirring and cooling in a water bath. When the reaction was complete the mixture was washed with water, dried and the solvent stripped off to give 8.2 g. of product.

EXAMPLE 9

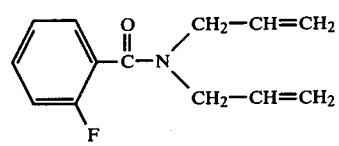

A solution was formed containing 4.5 g. of diallyl amine dissolved in 15 ml. of methylene chloride and 5.0 g. of triethylamine. Then, 7.1 g. of ortho-fluorobenzoyl chloride was added dropwise with stirring and cooling in a water bath. When the reaction was complete, the mixture was washed with water, dried and the solvent stripped off to give 8.5 g. of product.

EXAMPLE 10

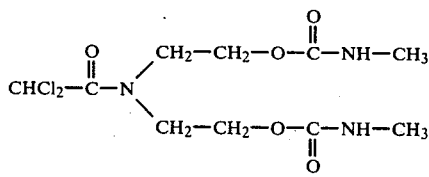

N,N-bis(2-hydroxyethyl) dichloroacetamide was prepared by reacting 26.3 g. of diethanolamine with 37 g. of dichloroacetyl chloride in the presence of 25.5 g. of triethylamine in 100 ml. of acetone. Then, 6.5 g. of the N,N-bis(2-hydroxyethyl) dichloroacetamide was dissolved in 50 ml. of acetone, then reacted with 4 g. of methyl isocyanate in the presence of dibutyl tin dilaurate and triethylamine catalysts. The reaction product was stripped under vacuum to yield 8.4 g. of product.

EXAMPLE 11

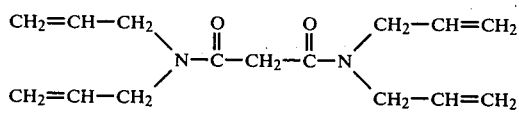

7.8 g. of diallyl amine was dissolved in 50 ml. of methylene chloride, with 8.5 g. of triethylamine added dropwise. Then, 5.6 g. of malonyl chloride was added dropwise with cooling and stirring. When the reaction was complete, the mixture was washed with water, dried over magnesium sulfate and stripped under vacuum to yield 7.0 g. of product.

EXAMPLE 12

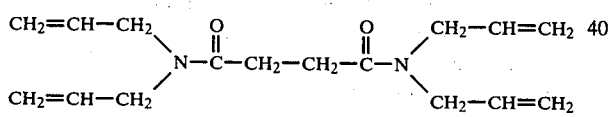

7.9 g. of diallyl amine was dissolved in 50 ml. of methylene chloride with 8.5 g. of triethylamine added dropwise. Then, 6.2 g. of succinyl chloride was added dropwise with cooling and stirring. When the reaction was complete, the mixture was washed with water, dried over magnesium sulfate and stripped under vacuum to yield 9.7 g. of product.

EXAMPLE 13

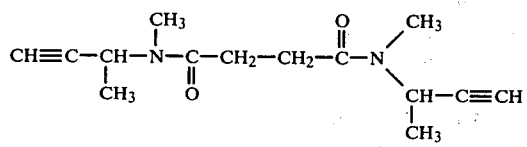

6.7 g. of N-methyl-1-methyl-3-propynylamine was dissolved in 50 ml. of methylene chloride with 8.5 g. of triethylamine added dropwise. Then, 6.2 g. of succinyl chloride was added dropwise with cooling and stirring. When the reaction was complete, the mixture was washed with water, dried over magnesium sulfate and stripped under vacuum to yield 7.0 g. of product.

EXAMPLE 14

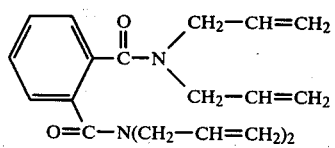

7.9 g. of diallyl amine was dissolved in 50 ml. of methylene chloride with 8.5 g. of triethylamine added dropwise. Then, 8.1 g. of o-phthaloyl chloride was added dropwise with cooling and stirring. When the reaction was complete, the mixture was washed with water, dried over magnesium sulfate and stripped under vacuum to yield 10.9 g. of product.

EXAMPLE 15

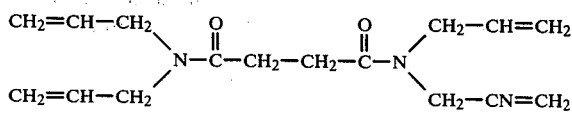

3.3 g. of N-methyl-1-methyl-3-propynylamine was dissolved in 50 ml. of methylene chloride with 4.5 g. of triethylamine added dropwise. Then, 9.2 g. of diphenyl acetyl chloride was added dropwise with cooling and stirring. When the reaction was complete, the mixture was washed with water, dried over magnesium sulfate and stripped under vacuum to yield 9.9 g. of the product.

EXAMPLE 16

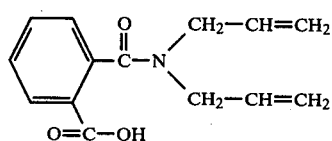

4.9 g. of diallyl amine was dissolved in 50 ml. of acetone with 7.4 g. of phthalic anhydride added portionwise with stirring. The solvent was stripped off under vacuum to yield 13.0 g. of product.

EXAMPLE 17

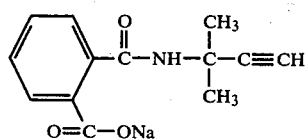

9.2 g. of N(1,1-dimethyl-3-propynyl)O-phthalamic acid was dissolved in 50 ml. of methanol and 9.6 g. of sodium methoxide. 25% in methanol was added portionwise with stirring and cooling. The solvent was stripped or removed under vacuum to yield 9.0 g. of product. The intermediate, N(1,1-dimethyl-3-propynyl)O-phthalamate was prepared from 29.6 g. of phthalic anhydride and 16.6 g. of 3-amino-3-methylbutyne in 150 ml. of acetone. The intermediate was precipitated with petroleum ether as a white solid and used without further purification.

EXAMPLE 18

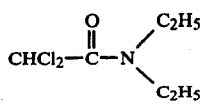

A 500 cc. 4-necked flask was provided with stirrer, thermometer and addition funnel. Then, 7.7 g. of diethylamine (0.105 mole), 4.0 g. of sodium hydroxide solution and 100 ml. of methylene chloride were charged to the flask and the mixture was cooled in a dry-ice-acetone bath. Then, 14.7 g. (0.10 mole) of dichloroacetyl chloride was added portionwise. The mixture was stirred for an additional hour and immersed in an ice bath. It was then phase separated and the lower organic phase was washed with two portions of 100 ml. of dilute hydrochloric acid, two 100 ml. of sodium carbonate solutions, dried over magnesium sulfate and concentrated under vacuum to yield 16.8 g. of product.

EXAMPLE 19

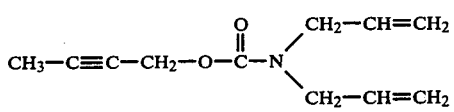

4.0 g. (0.025 mole) of N,N-diallylcarbamoyl chloride was added to 50 ml. of methylene dichloride. Then, 1.8 g. (0.025 mole) of 2-butyn-1-ol was added dropwise with 2.6 g. of triethylamine in 10 ml. methylene chloride. The reaction product was stirred at room temperature overnight, washed with water twice and dried over magnesium sulfate to yield 4.0 g. of product.

EXAMPLE 20

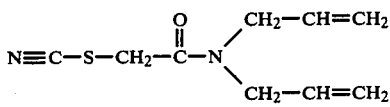

9.7 g. (0.1 mole) of potassium thiocyanate was dissolved in 100 ml. of acetone. Then, 8.7 g. (0.05 mole) of N,N-diallyl chloroacetamide were added at room temperature with 10 ml. of dimethyl formamide. The reaction product was stirred overnight. The reaction product was partially stripped. Water was added along with two portions of 100 ml. of ether. The ether was separated, dried and stripped to yield 7.2 g. of product.

EXAMPLE 21

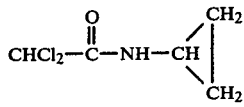

A solution of 50 ml. of benzene containing 7.4 g. (0.05 mole) of dichloro acetylchloride was formed. To this solution was added 3.0 g. (0.05 mole) of cyclopropylamine and 5.2 g. of triethylamine in 2 ml. of benzene at a temperature of 5°-10° C. A precipitate was formed and the mixture was stirred for two hours at room temperature and one hour at 50°-55° C. The product was worked-up as in previous examples to yield 5.7 g. of the product.

EXAMPLE 22

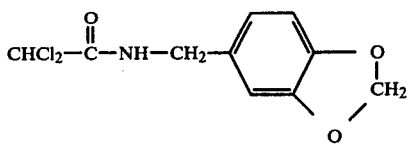

To 4.7 g. (0.032 mole) of piperonylamine and 1.2 g. of sodium hydroxide in 30 ml. of methylene chloride and 12 ml. of water was added 4.4 g. (0.03 mole) of dichloroacetyl chloride in 15 ml. of methylene chloride at −5° to 0° C. The mixture was stirred ten more minutes around 0° C., then allowed to warm to room temperature with stirring. The layers were separated and the organic layer washed with dilute hydrochloric acid, 10% sodium carbonate solution, water and dried to yield 5.9 g. of product.

EXAMPLE 23

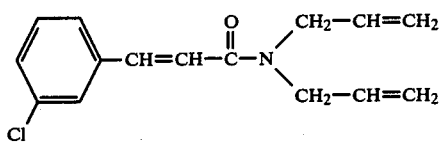

In a solution of 75 ml. of benzene containing 5.7 g. of meta-chlorocinnamyl chloride was formed. To this solution was added 3.2 g. of diallyl amine and 3.3 g. of triethyl amine in 2 ml. of benzene at a temperature of 5° to 10° C. A precipitate was formed and the mixture was stirred for two hours at room temperature and one hour at 55° C. The product was washed and worked up to yield 5.8 g. of product.

EXAMPLE 24

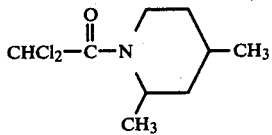

A 500 cc. 4-necked flask was provided with a stirrer, thermometer and addition funnel. Then, 11.9 g. 2,4-dimethylpiperidine, 4.0 g. of sodium hydroxide solution and 100 ml. of methylene chloride were charged to the flask and the mixture cooled in a dry-ice-acetone bath. Then, 14.7 g. (0.10 mole) of dichloroacetyl chloride were added in portions. The mixture was stirred for one hour and immersed in the ice bath, and then separated with the lower organic phase washed with two portions of 100 ml. of dilute hydrochloric acid and two portions of 100 ml. of 5% sodium carbonate solution, dried over magnesium sulfate and concentrated in a rotary evaporator under a water pump vacuum to yield 19.3 g. of product.

EXAMPLE 25

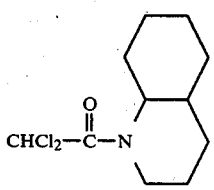

A 500 ml. 4-necked flask was provided with a stirrer, thermometer and addition funnel. Then, 14.6 g. (0.105 mole) of cis-trans-decahydroquinoline and 4.0 g. of sodium hydroxide solution and 100 ml. of methylene chloride were added together. Then, 14.7 g. of dichloroacetyl chloride was added portionwise. The reaction mixture was worked up by stirring for about an hour and immersed in an ice bath and then phase separated with the lower organic phase being washed with two portions of 100 ml. dilute hydrochloric acid, two portions of 100 ml. of 5% sodium carbonate, dried over magnesium sulfate and concentrated to yield 22.3 g. of product.

EXAMPLE 26

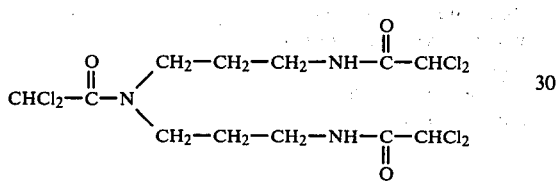

A 500 ml. 4-necked flask was provided with stirrer, thermometer and addition funnel. Then, 13.6 g. (0.104 mole) of 3,3'-iminobis-propylamine was added along with 12.0 g. of sodium hydroxide solution and 150 ml. of methylene chloride. Thereafter, the mixture was cooled in a dry ice-acetone bath and 44.4 g. (0.300 mole) of dichloroacetyl chloride was added portionwise. An oily product formed which was not soluble in methylene chloride and was separated and washed with two portions of 100 ml. of dilute hydrochloric acid and allowed to stand overnight. The next morning the product was washed with two portions of 100 ml. of 5% sodium carbonate and the product was taken up in 100 ml. of ethanol, dried over magnesium sulfate and concentrated to yield 21.0 g. of product.

EXAMPLE 27

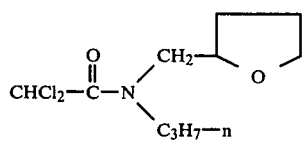

A 500 ml. 4-necked flask was provided with stirrer, thermometer and addition funnel. Then, 7.5 g. of tetrahydrofurfuryl-n-propylamine (0.0525 mole) and 2.0 g. sodium hydroxide solution and 100 ml. of methylene chloride were charged thereto. Then, 7.4 g. (0.05 mole) of dichloroacetyl chloride were added portionwise. The mixture was stirred for one additional hour in an ice bath and then separated with the lower organic phase washed with two portions of 100 ml. of dilute hydrochloric acid and two portions of 100 ml. of 5% sodium carbonate solution, dried over magnesium sulfate and concentrated to yield 12.7 g. of product.

EXAMPLE 28

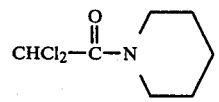

Example 27 was repeated in its entirety except that 8.9 g. of piperidine was used as the amine.

EXAMPLE 29

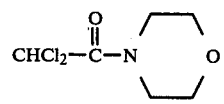

Example 28 was essentially repeated in its entirety except 9.1 g. of morpholine was used as the amine.

EXAMPLE 30

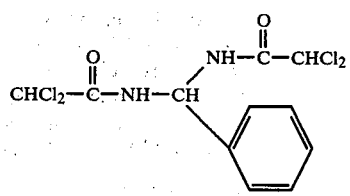

3.2 g. of benzaldehyde and 7.7 g. of dichloracetamide were combined with 100 ml. of benzene and approximately 0.05 g. of paratoluene sulfonic acid. The mixture was refluxed until water ceased to come over. On cooling the product crystallized from benzene yielding 7.0 g. of product.

EXAMPLE 31

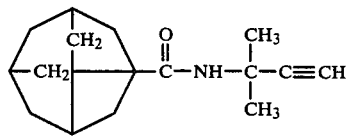

2.5 g. of 3-amino-3-methylbutyne was dissolved in 50 ml. of acetone and 3.5 g. of triethylamine was added, followed by 6.0 g. of adamantane-1-carbonyl chloride added dropwise with stirring and cooling. The mixture was poured into water and the solid product collected by filtration and dried under vacuum to give 6.5 g. of product.

EXAMPLE 32

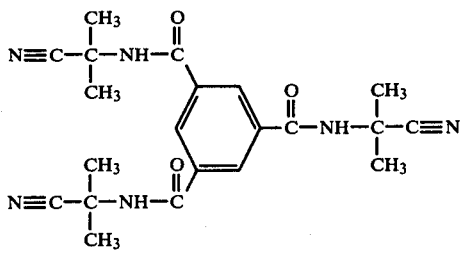

5.1 g. of 2-cyanoisopropylamine was dissolved in 50 ml. of acetone with 6.5 g. of triethylamine added, followed by 5.3 g. of benzene-1,3,5-tricarboxylic acid chloride added dropwise with stirring and cooling. The mixture was poured into water and the solid product collected by filtration and dried under vacuum to give 7.6 g. of product.

EXAMPLE 33

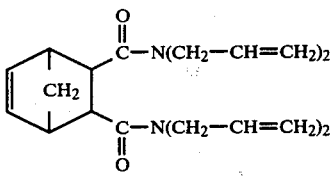

6.0 g. of diallylamine was dissolved in 50 ml. of methylene chloride, 6.5 g. of triethylamine was added and 6.6 g. of 3,6-endomethylene-1,2,3,6-tetrahydrophthaloyl chloride was added dropwise with stirring and cooling. When the reaction was complete the mixture was washed with water, dried over magnesium sulfate and stripped under vacuum to yield 9.3 g. of product.

EXAMPLE 34

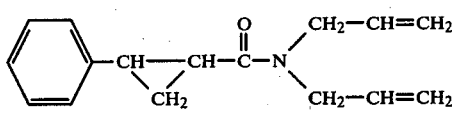

4.0 g. of diallylamine was dissolved in 50 ml. of methylene chloride, 4.5 g. of triethylamine was added and 7.2 g. of trans-2-phenylcyclopropane carbonyl chloride was added dropwise with cooling and stirring. When the reaction was complete the mixture was washed with water, dried over magnesium sulfate and stripped under vacuum to yield 9.3 g. of product.

EXAMPLE 35

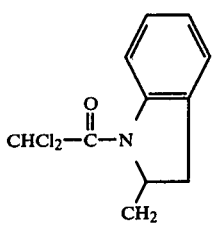

A solution was formed consisting of 4.0 g. (0.03 mole) of 2-methyl indoline, 7.0 ml. triethylamine and 100 ml. of methylene chloride. Then, 2.9 ml. of dichloroacetyl chloride was added thereto over a period of about one minute with dry ice cooling, keeping the temperature under 0° C. The solution was allowed to warm to room temperature and stand for one hour and then washed with water and then with dilute hydrochloric acid, dried over magnesium sulfate and evaporated to give a solid that was washed with n-pentane to give 5.0 g. of product.

EXAMPLE 36

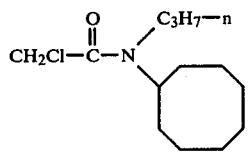

A 500 cc. 4-necked flask was provided with stirrer, thermometer and addition funnel. Then, 8.9 g. of cyclooctyl n-propylamine, 2.0 g. of sodium hydroxide solution and 100 ml. of methylene chloride were charged to the flask and the mixture was cooled in a dry ice-acetone bath. Then, 5.6 g. of chloroacetyl chloride was added portionwise. The mixture was stirred for about one additional hour, immersed in the ice bath, then phase separated and the lower organic phase was washed with two portions of 100 ml. of dilute hydrochloric acid and two portions of 100 ml. 5% sodium carbonate solution, dried over magnesium sulfate and concentrated to yield 9.5 g. of product.

EXAMPLE 37

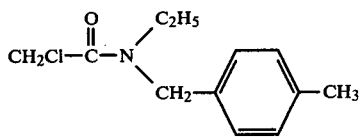

A 500 cc. 4-necked flask was provided with stirrer, thermometer and addition funnel. Then, 7.8 g. (0.0525 mole) of p-methylbenzyl ethylamine, 2.0 g. of sodium hydroxide solution and 100 ml. of methylene chloride were charged to the flask. The mixture was cooled in a dry ice-acetone bath. Then, 5.6 g. (0.05 mole) of chloroacetyl chloride was added portionwise. The mixture was stirred for about one additional hour, immersed in the ice bath, then phase separated with the lower organic phase being washed with two portions of 100 ml. of dilute hydrochloric acid and then two portions of 100 ml. of 5% sodium carbonate solution, dried over magnesium sulfate and concentrated to yield 9.5 g. of product.

EXAMPLE 38

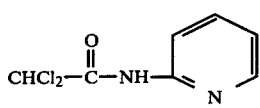

4.7 g. of amino pyridine were charged to a reaction vessel along with 100 ml. of acetone and stirred at 10°-15° C. Then, 7.0 ml. of triethylamine were added dropwise. Thereafter, 5.25 ml. of dichloroacetyl chloride in 10 ml. of acetone was added over a period of five minutes and stirred at room temperature. The solids were filtered off, washed with acetone to yield 10.0 g. of product.

EXAMPLE 39

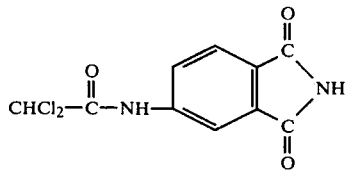

8.1 g. (0.05 mole) of 4-aminophthalimide was dissolved in 100 ml. of dimethylfuran, wherein 5.0 g. of dichloroacetyl chloride was stirred in at 0°–10° C. over a period of 5 minutes. Then, 7.0 ml. of triethylamine was added. The reaction mass was stirred for one-half hour at room temperature and then one liter of water was added. The reaction was filtered with water and dried to give 12.0 g. of product.

EXAMPLE 40

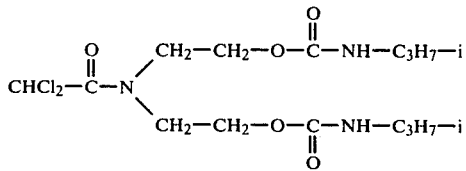

The compound of this example was prepared by reacting 5.4 g. of N,N-bis(2-hydroxyethyl) dichloroacetamide with 4.3 g. of isopropyl isocyanate in 50 ml. of acetone in the presence of dibutyltin dilaurate and triethylenediamine catalysts, to yield 8.2 g. of product.

EXAMPLE 41

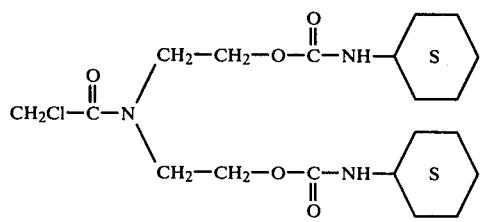

The compound of this example was prepared by reacting 3.6 g. of N,N-bis(2-hydroxyethyl) chloroacetamide with 5.0 g. of cyclohexyl isocyanate in the presence of 50 ml. of acetone and dibutyltin dilaurate and triethylenediamine catalysts. The reaction mass was heated to reflux and stripped under vacuum to yield 6.9 g. of product.

EXAMPLE 42

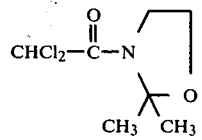

15 g. of acetone and 12.2 g. of ethanol amine were combined in 150 ml. of benzene and refluxed until no additional water came over. The resulting solution was examined and found to contain 2,2-dimethyl-1,3-oxazolidine. A quarter of the benzene solution (0.05 mole) was reacted with 7.4 g. of dichloroacetyl chloride and 5.5 g. of triethylamine, washed with water, dried and stripped under vacuum to give a light tan solid. A portion was recrystallized from ether giving a white product.

Other compounds were prepared in an analogous manner starting with the appropriate starting materials as outlined above. The following is a table of compounds representative of those embodied by the present invention. Compound numbers have been assigned to them and are used for identification throughout the balance of the specification.

TABLE I $$R-\overset{O}{\underset{\|}{C}}-N\overset{R_1}{\underset{R_2}{}}$$

| Compound No. | R | $R_1$ | $R_2$ |
|---|---|---|---|
| 1 | —CH(CH$_3$)Br | —CH$_2$—CH=CH$_2$ | —CH$_2$—CH=CH$_2$ |
| 2 | —C(CH$_3$)$_2$Br | " | " |
| 3 | —CCl$_2$—CH$_3$ | " | " |
| 4 | —CCl=CCl$_2$ | " | " |
| 5 | —CF$_2$—C$_2$F$_5$ | " | " |
| 6 | —CHCl$_2$ | " | " |
| 7 | —CH$_2$Cl | —CH$_2$—C≡N | —CH$_2$—C≡N |
| 8 | —CHCl$_2$ | —CH$_2$—CH=CH$_2$ | H |
| 9 | " | —C$_3$H$_7$ | —C$_3$H$_7$ |
| 10 | " | —C(CH$_3$)$_2$—C≡N | H |
| 11 | " | " | " |
| 12 | —CH$_2$Cl | —CH$_2$—CH=CH$_2$ | —CH$_2$—CH=CH$_2$ |
| 13 | —CCl$_3$ | " | " |
| 14 | " | —C(CH$_3$)$_2$—C≡CH | H |
| 15 | —CH$_2$Cl | —CH$_3$ | H |
| 16 | —CHCl$_2$ | " | —CH(CH$_3$)—C≡CH |
| 17 | —CCl$_3$ | —CH$_2$—CH=CH$_2$ | 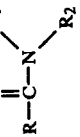 |
| 18 | —CHCl$_2$ | " | |
| 19 | " | H | 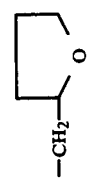 |
| 20 | —CH$_2$Cl | " | " |
| 21 | —CHCl$_2$ | " | 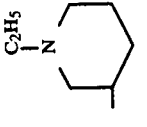 |
| 22 | —CH$_2$Cl | " | " |
| 23 | —CHCl$_2$ | " | 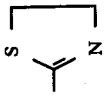 |
| 24 | —CHCl$_2$ | " | " |

TABLE I-continued $$R-\underset{\underset{O}{\|}}{C}-N\underset{R_2}{\overset{R_1}{<}}$$

| Compound No. | R | R₁ | R₂ |
|---|---|---|---|
| 25 | " | " | ![structure: -C(CH₃)=N-S- ring with isopropylidene] |
| 26 | " | " | ![structure: -C(CH₃)=N-N=S- ring] |
| 27 | " | " | ![benzothiazol-2-yl] |
| 28 | " | " | ![5-bromo-benzothiazol-2-yl] |
| 29 | $-\underset{\underset{O}{\|}}{C}-O-C_2H_5$ | —CH₃ | —CH(CH₃)—C≡CH |
| 30 | " | —CH₂—CH=CH₂ | —CH₂—CH=CH₂ |
| 31 | —CH₂—CH(CH₃)—CH₂—t-C₄H₉ | H | —C(CH₃)₂—C≡CH |
| 32 | —C(CH₃)₂—C₃H₇ | —CH₂—CH=CH₂ | —CH₂—CH=CH₂ |
| 33 | —CH₂—t-C₄H₉ | —CH₃ | —CH(CH₃)—C≡CH |
| 34 | " | H | —C(CH₃)₂—C≡N |
| 35 | —CH(CH₃)—C₃H₇ | —CH₂—CH=CH₂ | —CH₂—CH=CH₂ |
| 36 | " | —CH₃ | —CH(CH₃)—C≡CH |
| 37 | i-C₃H₇ | H | —CH(CH₃)—C≡CH |
| 38 | —C₁₃H₂₇ | —CH₃ | —CH(CH₃)C≡CH |
| 39 | —C₁₁H₂₃ | —CH₂—CH=CH₂ | —CH₂CH₂C≡CH |
| 40 | " | " | " |
| 41 | —C₉H₁₉ | H | —C(CH₃)₂—C≡CH |
| 42 | " | —CH₂—CH=CH₂ | —CH₂—CH=CH₂ |
| 43 | —C₆H₁₃ | H | —C(CH₃)₂—C≡CH |
| 44 | " | —CH₂—CH=CH₂ | —CH₂—CH=CH₂ |
| 45 | " | —CH₃ | —CH(CH₃)—C≡CH |
| 46 | —C₄H₉ | H | —C(CH₃)₂—C≡CH |
| 47 | " | " | " |

TABLE I-continued $$R-\overset{\overset{O}{\|}}{C}-N\overset{R_1}{\underset{R_2}{\diagdown}}$$

| Compound No. | R | $R_1$ | $R_2$ |
|---|---|---|---|
| 48 | —C$_3$H$_7$ | —CH$_2$—CH=CH$_2$ | —CH$_2$—CH=CH$_2$ |
| 49 | " | —CH$_3$ | —CH(CH$_3$)—C≡CH |
| 50 | " | H | —C(CH$_3$)$_2$C≡CH |
| 51 | —CH$_3$ | —CH$_2$—CH=CH$_2$ | —CH$_2$—CH=CH$_2$ |
| 52 | " | H | —C(CH$_3$)$_2$—C≡CH |
| 53 | —C(CH$_3$)=CH$_2$ | " | " |
| 54 | —CH=CH—CH$_3$ | —CH$_2$—CH=CH$_2$ | —CH$_2$—CH=CH$_2$ |
| 55 | " | H | —C(CH$_3$)$_2$—C≡CH |
| 56 | —CH=C(CH$_3$)$_2$ | —CH$_3$ | —CH(CH$_3$)—C≡CH |
| 57 | " | H | —C(CH$_3$)$_2$—C≡CH |
| 58 | —CH=CH—CH=CH—CH$_3$ | —CH$_2$—CH=CH$_2$ | —CH$_2$—CH=CH$_2$ |
| 59 | " | H | C(CH$_3$)$_2$C≡CH |
| 60 | 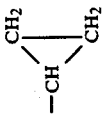 | —CH$_2$—CH=CH$_2$ | —CH$_2$—CH=CH$_2$ |
| 61 | " | —CH$_3$ | —CH(CH$_3$)—C≡CH |
| 62 | " | H | —C(CH$_3$)$_2$C≡CH |
| 63 | 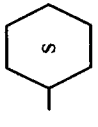 | —CH$_2$—CH=CH$_2$ | —CH$_2$—CH=CH$_2$ |
| 64 | " | —CH$_3$ | —CH(CH$_3$)—C≡CH |
| 65 | " | H | —C(CH$_3$)$_2$C≡CH |
| 66 | 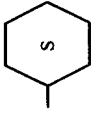—CH$_2$—CH$_2$— | —CH$_2$—CH=CH$_2$ | —CH$_2$—CH=CH$_2$ |
| 67 | " | —CH$_3$ | —CH(CH$_3$)—C≡CH |

TABLE I-continued $$R-\overset{O}{\underset{\|}{C}}-N\overset{R_1}{\underset{R_2}{\diagdown}}$$

| Compound No. | R | $R_1$ | $R_2$ |
|---|---|---|---|
| 68 | 2-fluorophenyl | $-CH_2-CH=CH_2$ | $-CH_2-CH=CH_2$ |
| 69 | " | $-CH_3$ | $-CH(CH_3)-C\equiv CH$ |
| 70 | " | H | $-C(CH_3)_2-C\equiv CH$ |
| 71 | 4-fluorophenyl | $-CH_2-CH=CH_2$ | $-CH_2-CH=CH_2$ |
| 72 | $-CH=CH_2$ | $-CH_3$ | $-CH(CH_3)-C\equiv CH$ |
| 73 | " | H | $-C(CH_3)_2-C\equiv CH$ |
| 74 | tetrahydrothiopyranyl-$CH_2-$ | $-CH_2-CH=CH_2$ | $-CH_2-CH=CH_2$ |
| 75 | " | H | $-C(CH_3)_2-C\equiv CH$ |
| 76 | " | $-CH_2-CH=CH_2$ | $-CH_2-CH=CH_2$ |
| 77 | 3-trifluoromethylphenyl | $-CH_3$ | $-CH(CH_3)-C\equiv CH$ |
| 78 | " | " | " |
| 79 | 2-iodophenyl | | |
| 80 | " | H | $-C(CH_3)_2-C\equiv CH$ |

TABLE I-continued $$R-\underset{\underset{O}{\parallel}}{C}-N\underset{R_2}{\overset{R_1}{\diagdown}}$$

| Compound No. | R | $R_1$ | $R_2$ |
|---|---|---|---|
| 81 | —CBr₃ | —CH₂—CH=CH₂ | —CH₂—CH=CH₂ |
| 82 | " | —CH₃ | —CH(CH₃)—C≡CH |
| 83 | " | H | —C(CH₃)₂—C≡CH |
| 84 | " | " | —C(CH₃)₂—C≡N |
| 85 | " | —CH₃ | —CH₂—CH=CH₂ |
| 86 | —CCl=CHCl | —CH₂CH=CH₂ | —CH(CH₃)C≡CH |
| 87 | —(CH₂)₄—CH₂—Br | —CH₃ | —CH₂CH=CH₂ |
| 88 | " | | —CH(CH₃)—C≡CH |
| 89 | 2-Cl-C₆H₄— | —CH₂—CH=CH₂ | —CH₂—CH=CH₂ |
| 90 | " | —CH₃ | —CH(CH₃)—C≡CH |
| 91 | " | " | " |
| 92 | 3-Cl-C₆H₄— | —CH₂CH=CH₂ | —CH₂CH=CH₂ |
| 93 | 4-Cl-C₆H₄— | —CH₃ | —CH(CH₃)—C≡CH |
| 94 | " | H | —C(CH₃)₂—C≡CH |
| 95 | 4-CH₃O-C₆H₄— | —CH₂—CH=CH₂ | —CH₂—CH=CH₂ |
| 96 | " | H | —C(CH₃)₂—C≡CH |

TABLE I-continued $$\underset{R}{\text{R}}-\overset{O}{\underset{\|}{C}}-\underset{}{N}\underset{R_2}{\overset{R_1}{\diagup}}$$

| Compound No. | R | $R_1$ | $R_2$ |
|---|---|---|---|
| 97 | 2-methoxyphenyl | —CH$_3$ | —CH(CH$_3$)—C≡CH |
| 98 | " | H | —C(CH$_3$)$_2$—C≡CH |
| 99 | 3,4,5-trimethoxyphenyl | —CH$_3$ | —CH(CH$_3$)—C≡CH |
| 100 | " | H | —C(CH$_3$)$_2$—C≡CH |
| 101 | 2-methylphenyl | —CH$_3$ | —CH(CH$_3$)—C≡CH |
| 102 | " | H | —C(CH$_3$)$_2$—C≡CH |
| 103 | 3-methylphenyl | —CH$_2$—CH=CH$_2$ | —CH$_2$—CH=CH$_2$ |
| 104 | 4-methylphenyl | —CH$_3$ | —CH(CH$_3$)—C≡CH |
| 105 | " | —CH$_2$—CH=CH$_2$ | —CH$_2$—CH=CH$_2$ |

TABLE I-continued $$R-\overset{O}{\underset{\|}{C}}-N\overset{R_1}{\underset{R_2}{\diagdown}}$$

| Compound No. | R | $R_1$ | $R_2$ |
|---|---|---|---|
| 106 | " | —CH₃ | —CH(CH₃)—C≡CH |
| 107 | " | H | —C(CH₃)₂—C≡CH |
| 108 | 2,4-dichlorophenyl | —CH₃ | —CH(CH₃)—C≡CH |
| 109 | 3,4-dichlorophenyl | H | —C(CH₃)₂—C≡CH |
| 110 | " | —CH₃ | —CH(CH₃)—C≡CH |
| 111 | 3-bromophenyl | —CH₂—CH=CH₂ | —CH₂—CH=CH₂ |
| 112 | furyl | —CH₃ | —CH(CH₃)—C≡CH |
| 113 | " | —CH₂—CH=CH₂ | —CH₂—CH=CH₂ |
| 114 | thienyl | H | —C(CH₃)₂—C≡CH |
| 115 | " | —CH₂—CH=CH₂ | —CH₂—CH=CH₂ |
| 116 | " | H | —C(CH₃)₂—C≡CH |
| 117 | —CHCl₂ | —C₂H₄OH | —C₂H₄OH |

TABLE I-continued $$R-\underset{\underset{O}{\|}}{C}-N\underset{R_2}{\overset{R_1}{<}}$$

| Compound No. | R | R₁ | R₂ |
|---|---|---|---|
| 118 | ″ | —CH₂—CH₂—O—C(=O)—CHCl₂ | —CH₂—CH₂—O—C(=O)—CHCl₂ |
| 119 | 2-furyl | —CH₂—CH₂—O—SO₂—CH₃ | —CH₂—CH—O—SO₂—CH₃ |
| 120 | 2-thienyl | —CH₃ | —CH(CH₃)—C≡CH |
| 121 | | ″ | ″ |
| 122 | —CHBr—CH₃ | H | —C(CH₃)₂—C≡CH |
| 123 | —CH₂—CH₂Cl | —CH₂—CH=CH₂ | —CH₂—CH=CH₂ |
| 124 | ″ | —CH₃ | —CH(CH₃)—C≡CH |
| 125 | ″ | H | —C(CH₃)₂—C≡CH |
| 126 | —CBr(CH₃)₂ | ″ | ″ |
| 127 | —CH₂I | —CH₂—CH=CH₂ | —CH₂—CH=CH₂ |
| 128 | ″ | —CH₃ | —CH(CH₃)—C≡CH |
| 129 | ″ | H | C(CH₃)₂—C≡CH |
| 130 | —CHCl₂ | —CH₂—CH₂Cl | —CH₂—CH₂Cl |
| 131 | ″ | —CH₂—CH₂—O—C(=O)—NH—CH₃ | —CH₂—CH₂—O—C(=O)—NH—CH₃ |
| 132 | ″ | —CH₂—CH₂—O—C(=O)—O—CH₃ | —CH₂—CH₂—O—C(=O)—O—CH₃ |
| 133 | ″ | —CH₂—CH₂—O—C(=O)—C₂H₅ | —CH₂—CH₂—O—C(=O)—C₂H₅ |
| 134 | ″ | —CH₂—CH₂—O—C(=O)—S—C₂H₅ | —CH₂—CH₂—O—C(=O)—S—C₂H₅ |
| 135 | ″ | | |

TABLE I-continued $$R-\overset{\overset{O}{\|}}{C}-N\overset{R_1}{\underset{R_2}{<}}$$

| Compound No. | R | R₁ | R₂ |
|---|---|---|---|
| 136 | —CH₂—C₆H₅ | —CH₂—CH=CH₂ | —CH₂—CH=CH₂ |
| 137 | " | —CH₃ | —CH(CH₃)—C≡CH |
| 138 | " | H | —C(CH₃)₂—C≡CH |
| 139 | —CH₂—CH₂—(cyclopentyl) | —CH₂—CH=CH₂ | —CH₂—CH=CH₂ |
| 140 | " | —CH₃ | —CH(CH₃)—C≡CH |
| 141 | —C₆H₅ | —CH₂—CH=CH₂ | —CH₂—CH=CH₂ |
| 142 | " | —CH₃ | —CH(CH₃)—C≡CH |
| 143 | —CH₂—C(=O)—N(CH₂—CH=CH₂)₂ | —CH₂—CH=CH₂ | —CH₂—CH=CH₂ |
| 144 | —CH₂—C(=O)—N(CH₃)—CH(CH₃)—C≡CH | —CH₃ | —CH(CH₃)—C≡CH |
| 145 | —CH₂—C(=O)—NH—C(CH₃)₂C≡CH | H | —C(CH₃)₂—C≡CH |
| 146 | —C(=O)—N(CH₂—CH=CH₂)₂ | —CH₂—CH=CH₂ | —CH₂—CH=CH₂ |
| 147 | —C(=O)—N(CH₃)—CH(CH₃)—C≡CH | —CH₃ | —CH(CH₃)—C≡CH |

TABLE I-continued $$R-\underset{\underset{R_2}{|}}{\overset{O}{\overset{\|}{C}}}-N\overset{R_1}{\underset{R_2}{}}$$

| Compound No. | R | R₁ | R₂ |
|---|---|---|---|
| 148 | $-\overset{O}{\overset{\|}{C}}-NH-C(CH_3)_2-C\equiv CH$ | H | $C(CH_3)_2-C\equiv CH$ |
| 149 | $-CH_2-CH_2-\overset{O}{\overset{\|}{C}}-N(CH_2-CH=CH_2)_2$ | $-CH_2-CH=CH_2$ | $-CH_2-CH=CH_2$ |
| 150 | $-CH_2-CH_2-\overset{O}{\overset{\|}{C}}-N(CH_3)-CH(CH_3)-C\equiv CH$ | $-CH_3$ | $-CH(CH_3)-C\equiv CH$ |
| 151 | $-(CH_2)_3-\overset{O}{\overset{\|}{C}}-N(CH_2-CH=CH_2)_2$ | $-CH_2-CH=CH_2$ | $-CH_2-CH=CH_2$ |
| 152 | $-(CH_2)_3-\overset{O}{\overset{\|}{C}}-N(CH_3)-CH(CH_3)-C\equiv CH$ | $-CH_3$ | $-CH(CH_3)-C\equiv CH$ |
| 153 | $-(CH_2)_4-\overset{O}{\overset{\|}{C}}-N(CH_2-CH=CH_2)_2$ | $-CH_2-CH=CH_2$ | $-CH_2-CH=CH_2$ |
| 154 | $-(CH_2)_4-\overset{O}{\overset{\|}{C}}-N(CH_3)-CH(CH_3)-C\equiv CH$ | $-CH_3$ | $-CH(CH_3)-C\equiv CH$ |
| 155 | $-C(CH_3)_2-\overset{O}{\overset{\|}{C}}-N(CH_3)-CH(CH_3)-C\equiv CH$ | " | " |
| 156 | $-CH_2-C(CH_3)_2-CH_2-\overset{O}{\overset{\|}{C}}-NH-C(CH_3)_3-C\equiv CH$ | H | $-C(CH_3)_2-C\equiv CH$ |
| 157 | $-CH_2-O-CH_2-\overset{O}{\overset{\|}{C}}-N(CH_2-CH=CH_2)_2$ | $-CH_2-CH=CH_2$ | $-CH_2-CH=CH_2$ |
| 158 | $-CH_2-O-CH_2-\overset{O}{\overset{\|}{C}}-N(CH_3)-CH(CH_3)-C\equiv CH$ | $-CH_3$ | $-CH(CH_3)-C\equiv CH$ |

TABLE I-continued $$R-\underset{\underset{O}{\|}}{C}-N\underset{R_2}{\overset{R_1}{\diagdown}}$$

| Compound No. | R | $R_1$ | $R_2$ |
|---|---|---|---|
| 159 | 2-methylphenyl-C(=O)-, with N(CH₂—CH=CH₂)₂ | —CH₂—CH=CH₂ | —CH₂—CH=CH₂ |
| 160 | 2-methylphenyl-C(=O)-, with N(CH₃)—CH(CH₃)—C≡CH | —CH₃ | —CH(CH₃)—C≡CH |
| 161 | 2-methylcyclohexenyl-C(=O)-NH—C(CH₃)₂—C≡CH | H | —C(CH₃)₂—C≡CH |
| 162 | 3-methylphenyl-C(=O)-, with N(CH₃)—CH(CH₃)—C≡CH | —CH₃ | —CH(CH₃)—C≡CH |
| 163 | 4-methylphenyl-C(=O)-, with N(CH₂CH=CH₂)₂ | —CH₂CH=CH₂ | —CH₂CH=CH₂ |
| 164 | —C(CH₃)₂—C(=O)—N(CH₂—CH=CH₂)₂ | —CH₂—CH=CH₂ | —CH₂—CH=CH₂ |

TABLE I-continued $$\underset{R_1}{\overset{O}{\underset{\|}{R-C-N}}}\diagdown{\overset{R_1}{\underset{R_2}{}}}$$

| Compound No. | R | $R_1$ | $R_2$ |
|---|---|---|---|
| 165 | $-C(CH_3)_2-\overset{O}{\overset{\|}{C}}-NH-C(CH_3)_2-C\equiv CH$ | H | $-C(CH_3)_2-C\equiv CH$ |
| 166 | " | $-CH_2-CH=CH_2$ | $-CH_2-CH=CH_2$ |
| 167 | 3-NO$_2$-C$_6$H$_4$- | H | $-C(CH_3)_2-C\equiv CH$ |
| 168 | " | $-CH_2-CH=CH_2$ | $-CH_2-CH=CH_2$ |
| 169 | 4-NO$_2$-C$_6$H$_4$- | $-CH_3$ | $-CH(CH_3)-C\equiv CH$ |
| 170 | " | H | $-C(CH_3)_2-C\equiv CH$ |
| 171 | " | $-CH_2-CH=CH_2$ | $-CH_2-CH=CH_2$ |
| 172 | C$_6$H$_5$-CHCl- | $-CH_3$ | $-CH(CH_3)-C\equiv CH$ |
| 173 | " | H | $-C(CH_3)_2-C\equiv CH$ |
| 174 | (C$_6$H$_5$)$_2$CH- | $-CH_3$ | $-CH(CH_3)-C\equiv CH$ |

TABLE I-continued $$\underset{R_2}{\overset{R_1}{\underset{|}{N}}}-\underset{\overset{\|}{O}}{C}-R$$

| Compound No. | R | $R_1$ | $R_2$ |
|---|---|---|---|
| 175 | 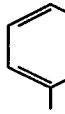 | —CH$_2$—CH=CH$_2$ | —CH$_2$—CH=CH$_2$ |
| 176 | 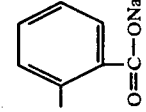 | H | —C(CH$_3$)$_2$C≡CH |
| 177 | " | " | " |
| 178 | 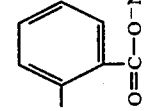 O=C—O—NH$_3^+$—C(CH$_3$)—C≡CH | | |
| 179 | —CHCl$_2$ | —C$_2$H$_5$ | —C$_2$H$_5$ |
| 180 | " | i-C$_3$H$_7$ | —CH$_2$—CH=CH$_2$ |
| 181 | " | —C$_3$H$_7$ | " |
| 182 | " | n-C$_4$H$_9$ | " |
| 183 | " | —CH$_2$—CH=CH$_2$ | —CH$_2$—CCl=CH$_2$ |
| 184 | " | —C$_3$H$_7$ | —CH$_2$—CH=CH$_2$ |
| 185 | " | i-C$_4$H$_9$ | " |
| 186 | " | —CH$_2$—C(CH$_3$)=CH$_2$ | " |
| 187 | " | n-C$_4$H$_9$ | sec-C$_4$H$_9$ |
| 188 | " | " | i-C$_4$H$_9$ |
| 189 | " | " | i-C$_3$H$_7$ |
| 190 | " | i-C$_4$H$_9$ | n-C$_3$H$_7$ |
| 191 | " | " | " |
| 192 | " | sec-C$_4$H$_9$ | " |
| 193 | " | n-C$_4$H$_9$ | —i-C$_4$H$_9$ |
| 194 | " | —C$_2$H$_5$ | |
| 195 | " | H |  |

TABLE I-continued $$R-\overset{O}{\underset{\|}{C}}-N\overset{R_1}{\underset{R_2}{}}$$

| Compound No. | R | $R_1$ | $R_2$ |
|---|---|---|---|
| 196 | " | $-CH_3$ | $-NH_2$ |
| 197 | Cl | $-CH_2-CH=CH_2$ | $-CH_2-CH=CH_2$ |
| 198 | $-CHCl_2$ | | |
| 199 | $-CH_2Cl$ | | |
| 200 | $-O-CH_2-C\equiv C-CH_3$ | $-CH_2-CH=CH_2$ | $=C[N(CH_3)_2]_2$ |
| 201 | $-O-C_2H_4Cl$ | " | $-CH_2-CH=CH_2$ |
| 202 | $-O-CH_2-CHCl_2$ | " | " |
| 203 | 4-Cl-C$_6$H$_4$-O- | " | " |
| 204 | $-CH_2-S-C\equiv N$ | " | " |
| 205 | $-CH_2-N(CH_2-CH=CH_2)_2$ | H | " |
| 206 | $-CHCl_2$ | $-CH_3$ | $-N(CH_3)-\overset{O}{\underset{\|}{C}}-CHCl_2$ |
| 207 | " | $-CH_2-CH=CH_2$ | $-N(\overset{O}{\underset{\|}{C}}-CHCl_2)_2$ |
| 208 | $-CH_2-\overset{O}{\underset{\|}{C}}-CH_3$ | " | $-CH_2-CH=CH_2$ |
| 209 | $-CH_2-C\equiv N$ | $-C_2H_5$ | " |
| 210 | $-CH_2-O-C\equiv N$ | | |
| 211 | $-CHCl_2$ | $-CH_2-CH_2-C\equiv N$ | $-CH_2-CH_2-O-\overset{O}{\underset{\|}{C}}-CHCl_2$ |
| 212 | " | | $-CH_2-CH-C\equiv N$ |
| 213 | " | H | C$_6$H$_5$- |

TABLE I-continued $$R-\overset{\overset{O}{\|}}{C}-N\overset{R_1}{\underset{R_2}{\diagdown}}$$

| Compound No. | R | $R_1$ | $R_2$ |
|---|---|---|---|
| 214 | " | " | 2-C₂H₅-C₆H₄ |
| 215 | " | " | 2,6-(CH₃)₂-C₆H₃ |
| 216 | " | " | 2,6-(i-C₃H₇)₂-C₆H₃ |
| 217 | —CH₂Cl | " | —CH₂—CH(CH₃)₂ |
| 218 | —CHCl₂ | " | cyclopropyl-CH₂— |
| 219 | " | " | i-C₄H₉ |
| 220 | —CH₂Cl | " | t-C₄H₉ |
| 221 | —CHCl₂ | " | t-C₄H₉ |
| 222 | —CH₂Cl | " | —CH(CH₃)—CH₂—CH(CH₃)—CH₃ |
| 223 | —CHCl₂ | " | 2-tetrahydrothiopyranyl |

TABLE I-continued $$R-\overset{O}{\underset{R_1}{C}}-N\overset{R_1}{\underset{R_2}{}}$$

| Compound No. | R | R₁ | R₂ |
|---|---|---|---|
| 224 | " | " | —CH₂—⟨phenyl⟩ |
| 225 | " | " | —CH₂—⟨4-Cl-phenyl⟩ |
| 226 | " | " | —CH₂—⟨3,4-diCl-phenyl⟩ |
| 227 | " | " | —CH₂—⟨3,4-methylenedioxyphenyl (O—CH₂—O)⟩ |
| 228 | —CH=CH—⟨3-F-phenyl⟩ | —CH₂—CH=CH₂ | —CH₂—CH=CH₂ |
| 229 | —CH=CH—⟨4-CH₃-phenyl⟩ | " | " |
| 230 | —CH=CH—⟨4-F-phenyl⟩ | " | " |

TABLE I-continued $$\underset{R_1}{\overset{O}{\underset{\|}{R-C-N}}}\overset{R_1}{\underset{R_2}{}}$$

| Compound No. | R | R₁ | R₂ |
|---|---|---|---|
| 231 | 3-Cl-C₆H₄-CH=CH- | | |
| 232 | -CHCl₂ | | " |
| 233 | " | -t-C₄H₉ | -CH=CH-CH₂-CH₃ |
| 234 | " | -C(CH₃)₂-C≡CH | " |
| 235 | " | -C₂H₅ | (CH₂-CH₃)(CH-CH₃)C= |
| 236 | " | n-C₄H₉ | -CH=CH-CH₂-CH₃ |
| 237 | " | cyclohexenyl | n-C₃H₇ |
| 238 | " | -C(CH₃)=CH-CH₂-CH₃ | " |
| 239 | -CH₂-SO₂-N(CH₂-CH=CH₂) | -CH₂-CH=CH₂ | -CH₂-CH=CH₂ |
| 240 | -CH(S-C₂H₅)₂ | -CH₃ | -N=C(CH₃)₂ |
| 241 | -CHCl₂ | -CH₂-CH=CH₂ | -CH₂-CH=CH₂ |
| 242 | -CH₂-O-C(=O)-CHCl₂ | " | " |
| 243 | 4-Cl-C₆H₄-CH(Cl)₂- | sec-C₄H₉ | -C₂H₅ |
| 244 | -CHCl₂ | t-C₄H₉ | " |
| 245 | " | | |

TABLE I-continued $$\underset{R_1}{\overset{O}{\underset{\|}{R-C-N}}}\underset{R_2}{\overset{R_1}{\diagdown}}$$

| Compound No. | R | $R_1$ | $R_2$ |
|---|---|---|---|
| 246 | " | sec-$C_5H_{11}$ | " |
| 247 | " | i-$C_3H_7$ | " |
| 248 | " | —$CH_3$ | tetrahydropyran-yl (S ring with CH) |
| 249 | " | —$C_2H_5$ | " |
| 250 | " | n-$C_3H_7$ | —$CH_2$—(3-methylphenyl with additional $CH_3$) |
| 251 | " | $CH_3$ | sec-$C_5H_{11}$ |
| 252 | " | n-$C_3H_7$ | " n-$C_5H_{11}$ |
| 253 | " | n-$C_3H_7$ | n-$C_4H_9$ |
| 254 | " | i-$C_4H_9$ | sec-$C_4H_9$ |
| 255 | " | $CH_3$ | i-$C_3H_7$ |
| 256 | " | " | —CH($CH_3$)—CH($CH_3$)—$CH_3$ |
| 257 | " | —$C_2H_5$ | (S-ring with two $CH_3$ groups) |
| 258 | " | " | (S-ring with $CH_3$) |
| 259 | " | " | (S-ring with $CH_3$) |

TABLE I-continued $$R-\overset{\overset{\displaystyle O}{\|}}{C}-N\overset{R_1}{\underset{R_2}{}}$$

| Compound No. | R | $R_1$ | $R_2$ |
|---|---|---|---|
| 260 | " | —CH₃ | sec-C₄H₉ |
| 261 | " | —C₂H₅ | n-C₆H₁₃ |
| 262 | " | n-C₃H₇ | t-C₄H₉ |
| 263 | " | " | —CH(CH₃)—CH(CH₃)—CH₃ |
| 264 | " | " | cyclopentyl |
| 265 | " | " | —CH₂—C₆H₄—CH₃ (4-methyl) |
| 266 | " | " | —CH₂—C₆H₃(CH₃)₂ (2,4-dimethyl) |
| 267 | " | " | —CH₂—C₆H₄—Cl (3-chloro) |
| 268 | " | —C₂H₅ | 3,5-dimethylcyclohexyl |

TABLE I-continued $$\underset{R_1}{\overset{O}{\underset{\|}{R-C-N}}}\overset{R_2}{}$$

| Compound No. | R | $R_1$ | $R_2$ |
|---|---|---|---|
| 269 | " | | cyclohexyl with 1,3-(CH$_3$)$_2$ |
| 270 | " | | cyclohexyl with 1,2-(CH$_3$)$_2$ |
| 271 | " | | cyclohexyl with CH$_3$, C$_2$H$_5$ |
| 272 | " | | cyclohexyl with C$_2$H$_5$, CH$_3$ |
| 273 | " | | cyclohexyl-CH(CH$_3$)$_2$ |
| 274 | " | | cyclohexyl-C$_3$H$_7$ |

TABLE I-continued
$$R-\overset{O}{\underset{\|}{C}}-N\overset{R_1}{\underset{R_2}{\diagdown}}$$
| Compound No. | R | $R_1$ | $R_2$ |
|---|---|---|---|
| 275 | " |  | cyclohexyl-CH$_3$ |
| 276 | " | | cyclohexyl-CH$_3$ |
| 277 | " | | CH$_3$-cyclohexyl |
| 278 | " | | cyclohexyl-C$_2$H$_5$ |
| 279 | " | | C$_2$H$_5$-cyclohexyl-CH$_3$ |
| 280 | " | | cyclohexyl-C$_2$H$_5$ |

TABLE I-continued $$R-\overset{\overset{O}{\|}}{C}-N\overset{R_1}{\underset{R_2}{\diagdown}}$$

| Compound No. | R | $R_1$ | $R_2$ |
|---|---|---|---|
| 281 | " | —CH$_3$ | —CH$_2$—C$_6$H$_4$(2-Cl) |
| 282 | " | " | —CH$_2$—C$_6$H$_4$(3-Cl) |
| 283 | " | " | —CH$_2$—C$_6$H$_4$(4-Cl) |
| 284 | " | —C$_2$H$_5$ | —CH$_2$—C$_6$H$_3$(2-CH$_3$, 4-CH$_3$) |
| 285 | " | n-C$_3$H$_7$ | " |
| 286 | " | | decahydronaphthyl |

TABLE I-continued
$$\underset{R}{}-\underset{\parallel}{C}-\underset{R_1}{N}-R_2$$
| Compound No. | R | R₁ | R₂ |
|---|---|---|---|
| 287 | " | H |  (2-methyldecahydronaphthalene) |
| 288 | " | —C₂H₅ | —CH₂—CH₂—N(C₂H₅)—C(O)—CHCl₂ |
| 289 | " | —C₃H₆—NH—C(O)—CHCl₂ | " |
| 290 | " | 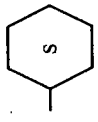 (phenyl) | —C₃H₆—NH—C(O)—CHCl₂ |
| 291 | " | —CH₂—CH=CH₂ | —CH₂—C(O)—O—C₂H₅ |
| 292 | " | —C₂H₅ | 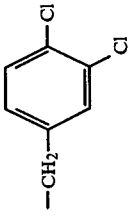 (tetrahydrothiopyranyl) |
| 293 | " | n-C₃H₅ | " |
| 294 | " | | 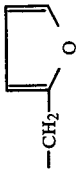 (3,4-dichlorobenzyl) |
| 295 | " | —CH₂—(furyl) | n-C₃H₇ |

TABLE I-continued $$R-\underset{\underset{O}{\|}}{C}-N\underset{R_2}{\overset{R_1}{<}}$$

| Compound No. | R | R₁ | R₂ |
|---|---|---|---|
| 296 | " | | cycloheptyl-CH₃ |
| 297 | " | n-C₃H₇ | " |
| 298 | " | " | n-C₆H₁₃ |
| 299 | " | —C₂H₄—O—CH₃ | —C₂H₄—O—CH₃ |
| 300 | " | —C₂H₄—O—C₂H₅ | —C₂H₄—O—C₂H₅ |
| 301 | " | —C₂H₅ | —CH₂—C₆H₅ |
| 302 | " | n-C₃H₇ | " |
| 303 | " | i-C₃H₇ | " |
| 304 | " | n-C₄H₉ | " |
| 305 | " | " | 1-C₂H₅-4-C₂H₅-cyclohexenyl |
| 306 | " | | 3,5-dimethylcyclohexyl |
| 307 | " | | cyclohexyl |

TABLE I-continued
$$\underset{R_1}{\overset{O}{\underset{\|}{R-C-N}}}\underset{R_2}{\overset{R_1}{\diagdown}}$$
| Compound No. | R | $R_1$ | $R_2$ |
|---|---|---|---|
| 308 | " | | 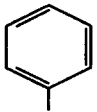 |
| 309 | " | —CH₃ | 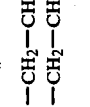 |
| 310 | " | —C₂H₅ | " |
| 311 | " | n-C₃H₇ | " |
| 312 | " | i-C₃H₇ | " |
| 313 | " | n-C₄H₉ | " |
| 314 | " | sec-C₄H₉ | " |
| 315 | " | t-C₄H₉ | " |
| 316 | " | —CH₃ | —CH₂—CH₂OH |
| 317 | " | | —CH₂—CH₂—C≡N |
| 318 | " | n-C₆H₁₃ | n-C₆H₁₃ |
| 319 | " | —CH₃ | —CH₂—CH₂OH |
| 320 | " | | 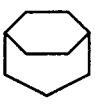 |
| 321 | " | —CH₂—CH₂—SH | 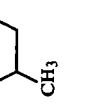 |
| 322 | " | H | 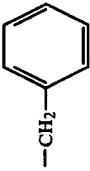 |
| 323 | —CH₂Cl | " | —C(C₂H₅)₂—C≡N |

TABLE I-continued $$\underset{R_1}{\overset{O}{\underset{\|}{R-C-N}}}\overset{R_2}{}$$

| Compound No. | R | $R_1$ | $R_2$ |
|---|---|---|---|
| 324 | —CHCl$_2$ | " | 2-Cl-C$_6$H$_4$ |
| 325 | " | " | 2-CF$_3$-C$_6$H$_4$ |
| 326 | " | " | 2,5-(CH$_3$)$_2$-C$_6$H$_3$ |
| 327 | —CH$_2$Cl | " | " |
| 328 | —CHCl$_2$ | " | 2,6-Cl$_2$-C$_6$H$_3$ |
| 329 | " | " | 2,6-(C$_2$H$_5$)$_2$-C$_6$H$_3$ |

TABLE I-continued $$R-\underset{\underset{O}{\|}}{C}-N\underset{R_2}{\overset{R_1}{<}}$$

| Compound No. | R | $R_1$ | $R_2$ |
|---|---|---|---|
| 330 | " | " | 2-ethoxyphenyl |
| 331 | " | " | 3,5-dimethylphenyl |
| 332 | " | " | $-CH_2-C(CH_3)=CH_2$ |
| 333 | $-CH_2Cl$ | " | $-CH_2-CH_2-O-CH_3$ |
| 334 | $-CHCl_2$ | " | $-CH_2-CH_2-O-CH_3$ |
| 335 | " | " | phenyl |
| 336 | $-CH_2Cl$ | $-CH_3$ | $-CH_2-CH_2$—phenyl |
| 337 | $-CHCl_2$ | " | $-CH_2-C\equiv CH$ |
| 338 | " | H | $-CH_2-C\equiv CH$ |
| 339 | " | " | tetrahydrothiopyran-CH$_2$— |
| 340 | " | " | $-CH_2-CH_2-N(C_2H_5)_2$ |
|  |  |  | $-CH_2-CH(OCH_3)_2$ |
| 341 | " | " | $-CH_2-CH_2-NHC(=O)-CHCl_2$ |

TABLE I-continued $$\underset{R-C-N}{\overset{O}{\parallel}}\overset{R_1}{\underset{R_2}{\diagdown}}$$

| Compound No. | R | $R_1$ | $R_2$ |
|---|---|---|---|
| 342 | -CH=CH-（2-F-C₆H₄） | -CH₂-CH=CH₂ | -CH₂-CH=CH₂ |
| 343 | -CHCl₂ | H | -CH(NH-CO-CHCl₂)-C₆H₅ |
| 344 | " | " | -CH(NH-CO-CHCl₂)-（3-NO₂-C₆H₄） |
| 345 | " | " | -CH(CH=CH₂)-NH-CO-CHCl₂ |
| 346 | " | " | -CH(NH-CO-CH₂Cl)-C₆H₅ |
| 347 | " | " | -CH(NH-CO-CH₂Cl)-（3-NO₂-C₆H₄） |
| 348 | " | " | -CH(NH-CO-CHCl₂)-（2,6-Cl₂-C₆H₃） |

TABLE I-continued $$R-\overset{O}{\underset{\|}{C}}-N\overset{R_1}{\underset{R_2}{\diagdown}}$$

| Compound No. | R | R₁ | R₂ |
|---|---|---|---|
| 349 | (thietanyl, S-containing 4-membered ring with attachment) | " | —C(CH₃)₂—C≡N |
| 350 | (tricyclic cage structure with CH₂ groups) | " | —C(CH₃)₂—C≡CH |
| 351 | (1,3-benzene-dicarbonyl with 5-methyl, both C(=O)—N(CH₂—CH=CH₂)₂) | " | —C(CH₃)₂—C≡N |
| 352 | (1,3-benzene-dicarbonyl with 5-methyl, both C(=O)—N(CH₂—CH=CH₂)₂) | —CH₂—CH=CH₂ | —CH₂—CH=CH₂ |
| 353 | (1,3-benzene-dicarbonyl with 5-methyl, both C(=O)—NH—C(CH₃)₂C≡N) | H | —C(CH₃)₂—C≡N |
| 354 | —CH(OCH₃)(phenyl) | —CH₂—CH=CH₂ | —CH₂—CH=CH₂ |

TABLE I-continued $$R-\overset{\overset{O}{\|}}{C}-N\overset{R_1}{\underset{R_2}{\diagdown}}$$

| Compound No. | R | $R_1$ | $R_2$ |
|---|---|---|---|
| 355 | —CH(O—C(=O)—CH$_3$)—C$_6$H$_5$ | H | —C(CH$_3$)$_2$—C≡CH |
| 356 | " | —CH$_2$—CH=CH$_2$ | —(CH$_3$)$_2$—C≡N |
| 357 | 6-methyl-2-pyridyl-C(=O)—N(CH$_2$—CH=CH$_2$)$_2$ | —CH$_2$—CH=CH$_2$ | —CH$_2$—CH=CH$_2$ |
| 358 | 6-methyl-2-pyridyl-C(=O)—NH—C(CH$_3$)$_2$C≡CH | " | " |
| 359 | (CH$_2$=CH—CH$_2$)—N—C(=O)—(2-methylcyclohexyl) | H | —C(CH$_3$)$_2$—C≡CH |
| 360 | HC≡C—C(CH$_3$)$_2$—NH—C(=O)—(2-methylcyclohexyl) | —CH$_2$—CH=CH$_2$ | —CH$_2$—CH=CH$_2$ |
| 361 | 2-phenylthiiranyl | H | —C(CH$_3$)$_2$—C≡CH |
| 362 | " | " | —(CH$_3$)$_2$—C≡CH |
| 363 | —CH$_2$—CH$_2$—C(=O)—O—CH$_3$ | " | —C(CH$_3$)=CH—C≡N |
| 364 | —CHCl$_2$ | | |

TABLE I-continued $$\underset{R_1}{R}-\underset{\|}{C}-\underset{R_2}{N}$$

| Compound No. | R | R₁ | R₂ |
|---|---|---|---|
| 365 | [4-methyl-1,3-dithiolan-2-yl] | —CH₂—CH=CH₂ | —CH₂—CH=CH₂ |
| 366 | —CHCl₂ | H | [2-methylphenyl]NH—C(=O)—CHCl₂ |
| 367 | " | [2-methyl-2,3-dihydro-1H-inden-2-yl] | |
| 368 | CHCl₂ | —C(=O)—CH₃ | —CH₂—CH(CH₃)₂ |
| 369 | " | —CHO | " |
| 370 | 3-chlorophenyl | H | —C(CH₃)₃ |
| 371 | —CH=CH—phenyl | | " |

TABLE I-continued $$R-\overset{O}{\underset{\|}{C}}-N\overset{R_1}{\underset{R_2}{\diagdown}}$$

| Compound No. | R | $R_1$ | $R_2$ |
|---|---|---|---|
| 372 | 2-furyl | " | $-C(CH_3)_2-C\equiv CH$ |
| 373 | 2-thienyl | $CH_3$ | $-CH(CH_3)-C\equiv CH$ |
| 374 | 4-fluorophenyl | H | $-C(CH_3)_2-C\equiv N$ |
| 375 | $-CH_2-$(2-thienyl) | " | " |
| 376 | $-CH_2-C(CH_3)_3$ | " | $-C(CH_3)_2-C\equiv N$ |
| 377 | $-CH(C_2H_5)-$phenyl | " | $-C(CH_3)_2-C\equiv CH$ |
| 378 | $-CH=$(4-methylphenyl) | " | " |
| 379 | $-CH=$(3,5-dimethoxyphenyl) | " | $-C(CH_3)_2-C\equiv CH$ |

TABLE I-continued $$R-\overset{\overset{O}{\|}}{C}-N\overset{R_1}{\underset{R_2}{<}}$$

| Compound No. | R | $R_1$ | $R_2$ |
|---|---|---|---|
| 380 | —CH=CH—C₆H₅ | " | —C(CH₃)₂—C≡N |
| 381 | " | —CH₃ | —CH(CH₃)—C≡CH |
| 382 | " | H | —(CH₃)₂—C≡CH |
| 383 | —CH=CH—C₆H₄Cl (p) | " | —C(CH₃)₂—C≡N |
| 384 | —(CH₃)=CH—C₆H₅ | " | 2,6-diethylphenyl |
| 385 | H | —CH₂—CH=CH₂ | tetrahydrofuran-2-yl |
| 385 | —CH₂—O—C(O)—CCl=CCl—CCl=CCl | —CH₂—CH=CH₂ | —CH₂—CH=CH₂ |
| 386 | —CHCl₂ | H | —CH₂—CH=CH₂ |
| 387 | —CH₂Cl | H | —CH₂—NH—C(O)—CH₂—O—(2,4-dichlorophenyl) |

TABLE I-continued $$R-\overset{O}{\overset{\parallel}{C}}-N\overset{R_1}{\underset{R_2}{\diagdown}}$$

| Compound No. | R | $R_1$ | $R_2$ |
|---|---|---|---|
| 388 | —CCl$_3$ | | —CH$_2$—NH—$\overset{O}{\overset{\parallel}{C}}$—CH$_2$Cl |
| 389 | —CHCl$_2$ | " | 3-hydroxyphenyl (m-tolyl with OH) |
| 390 | " | " | 3-methylphenyl-O-$\overset{O}{\overset{\parallel}{C}}$—NH—C$_2$H$_5$ |
| 391 | " | " | 3-methylphenyl-O-$\overset{O}{\overset{\parallel}{C}}$—NH—CH$_2$—CH=CH$_2$ |
| 392 | " | " | —$\overset{O}{\overset{\parallel}{C}}$—O—C$_2$H$_5$ |
| 393 | " | " | —$\overset{O}{\overset{\parallel}{C}}$—O—C$_2$H$_4$Cl |
| 394 | CH$_3$ | " | —C(CF$_3$)$_2$—OH |
| 395 | —CHCl$_2$ | " | 3-methylphenyl-NH—$\overset{O}{\overset{\parallel}{C}}$—CHCl$_2$ |

TABLE I-continued $$R-\overset{O}{\underset{\|}{C}}-N\overset{R_1}{\underset{R_2}{\diagdown}}$$

| Compound No. | R | $R_1$ | $R_2$ |
|---|---|---|---|
| 396 | " | " | 3-methylphenyl-NH-C(=O)-C$_2$H$_5$ |
| 397 | -CH$_2$-O-C(CHCl$_2$)$_2$-OH | -CH$_2$-CH=CH$_2$ | -CH$_2$-CH=CH$_2$ |
| 398 | -CH$_2$-O-C(CHCl$_2$)$_2$(CCl$_3$)-OH | " | " |
| 399 | -CH$_2$Cl | H | 3,5-dichlorophenyl-CH$_2$-NH-C(=O)-CH$_2$Cl |
| 400 | 2,4-dichlorophenoxy | " | 3-(CH=CH-C(=O)-C(CH$_3$)$_3$)phenyl |
| 401 | 2,4-dichloro-methylphenyl | " | 3-(CH=CH-C(=O)-C(CH$_3$)$_3$)phenyl |
| 402 | -CH$_2$Cl | n-C$_4$H$_9$ | -CH=CH$_2$ |

TABLE I-continued $$\underset{R_2}{\overset{R_1}{\underset{|}{N}}}$$
$$R-\overset{O}{\underset{\|}{C}}-N$$

| Compound No. | R | $R_1$ | $R_2$ |
|---|---|---|---|
| 403 | $-C(C-O-CH_3)=C(CH_3)-OH$ with =O on first C | H | 3,5-dichlorophenyl |
| 404 | $-CH_2Cl$ | $-CH_3$ | $-CH_2-CH_2-C\equiv N$ |
| 405 | " | $n-C_6H_{13}$ | $n-C_6H_{13}$ |
| 406 | " | $-C_2H_5$ | phenyl |
| 407 | " | $n-C_3H_7$ | $-CH_2-$phenyl |
| 408 | " | $i-C_3H_7$ | " |
| 409 | " | $-CH_3$ | $-CH_2-$(3-chlorophenyl) |
| 410 | " | " | $-CH_2-$(4-chlorophenyl) |

TABLE I-continued
$$R-\overset{O}{\underset{\|}{C}}-N\overset{R_1}{\underset{R_2}{}}$$
| Compound No. | R | $R_1$ | $R_2$ |
|---|---|---|---|
| 411 | " | $-C_2H_5$ | 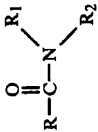 (2,5-dimethylbenzyl) |
| 412 | " | n-$C_3H_7$ |  (cyclopentyl) |
| 413 | " | " |  (decahydronaphthyl) |
| 414 | " | " | 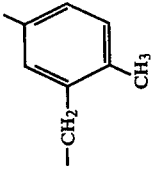 (1,4-diethylcyclohexyl) |
| 415 | " | " | 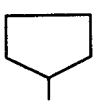 (methylcyclohexyl) |
| 416 | " | $-CH_3$ | i-$C_3H_7$ |
| 417 | " | " | $-CH(CH_3)-CH(CH_3)-CH_3$ |

TABLE I-continued $$\underset{R_2}{\overset{R_1}{\underset{|}{N}}}-\underset{\overset{||}{O}}{C}-R$$

| Compound No. | R | $R_1$ | $R_2$ |
|---|---|---|---|
| 418 | " | —$C_2H_5$ | *p*-$CH_3C_6H_4$— |
| 419 | " | n-$C_3H_7$ | i-$C_4H_9$ |
| 420 | " | " | sec-$C_5H_{11}$ |
| 421 | " | " | t-$C_4H_9$ |
| 422 | " | i-$C_4H_9$ | sec-$C_4H_9$ |
| 423 | " | —$C_2H_5$ | " |
| 424 | $CH_2Cl$ | i-$C_4H_9$ | i-$C_3H_7$ |
| 425 | " | n-$C_4H_9$ | i-$C_4H_9$ |
| 426 | " | —$CH_2$—$CH_2$—O—$CH_3$ | —$CH_2$—$CH_2$—O—$CH_3$ |
| 427 | " | —$CH_2$—$CH_2$—O—$C_2H_5$ | —$CH_2$—$CH_2$—O—$C_2H_5$ |
| 428 | " | tetrahydrofurfuryl-$CH_2$— | n-$C_3H_7$ |
| 429 | " | furfuryl-$CH_2$— | " |
| 430 | " | n-$C_3H_7$ | 3,4-dichlorobenzyl |
| 431 | " | " | 2,4-dichlorobenzyl |
| 432 | " | " | " |

TABLE I-continued $$R-\underset{\underset{O}{\|}}{C}-N\underset{R_2}{\overset{R_1}{<}}$$

| Compound No. | R | $R_1$ | $R_2$ |
|---|---|---|---|
| 433 | " | " | cycloheptyl-CH- |
| 434 | " | $-C_2H_5$ | 3-Cl-C6H4-CH2- |
| 435 | " | " | 2,4-(CH3)2-C6H3-CH2- |
| 436 | " | n-$C_3H_7$ | 3-CH3-C6H4-CH2- |
| 437 | " | $-C_2H_5$ | 4-CH3-C6H4-CH2- |
| 438 | " | $-CH_3$ | 3-CH3-C6H4-CH2- |
| 439 | $-CHCl_2$ | " | " |

TABLE I-continued $$R-\underset{\underset{O}{\|}}{C}-N\underset{R_2}{\overset{R_1}{\diagdown}}$$

| Compound No. | R | $R_1$ | $R_2$ |
|---|---|---|---|
| 440 | " | —$C_2H_5$ | —$CH_2$—C$_6$H$_4$—CH$_3$ (p) |
| 441 | " | n-$C_3H_7$ | —$CH_2$—C$_6$H$_4$—CH$_3$ (m) |
| 442 | " | —$C_2H_5$ | —$CH_2$—C$_6$H$_3$(CH$_3$)$_2$ |
| 443 | " | " | —$CH_2$—C$_6$H$_4$—Cl (m) |
| 444 | —$CH_2Cl$ | —$CH_3$ | n-$C_4H_9$ |
| 445 | —$CHCl_2$ | " | sec-$C_4H_9$ |
| 446 | —$CH_2Cl$ | " | " |
| 447 | —$CHCl_2$ | " | n-$C_3H_7$ |
| 448 | —$CH_2Cl$ | " | t-$C_4H_9$ |
| 449 | —$CHCl_2$ | " | sec-$C_4H_9$ |
| 450 | —$CH_2Cl$ | n-$C_4H_9$ | " |
| 451 | —$CHCl_2$ | i-$C_3H_7$ | " |
| 452 | —$CH_2Cl$ | " | n-$C_5H_{11}$ |
| 453 | —$CHCl_2$ | " | " |
| 454 | —$CH_2Cl$ | " | sec-$C_5H_{11}$ |
| 455 | —$CHCl_2$ | " | " |
| 456 | " | H | —CH$_2$-pyridyl |

TABLE I-continued $$\underset{R_1}{\overset{O}{\underset{\parallel}{R-C-N}}}\overset{R_1}{\underset{R_2}{}}$$

| Compound No. | R | $R_1$ | $R_2$ |
|---|---|---|---|
| 457 | " | " | 4-pyridyl |
| 458 | " | " | 2-methyl-pyridyl |
| 459 | " | " | CH₃-C=CH-C(CH₃)=N-O (isoxazole) |
| 460 | " | " | phthalimido (benzo-isoindoline-1,3-dione NH) |
| 461 | " | —CH₂—O—CH₃ | 2,6-diethylphenyl |
| 462 | " | H | —C(CH₃)=CH—C(O)—O—C₂H₅ |
| 463 | " | " | —NH—C(O)—CHCl₂ |

TABLE I-continued $$\underset{R_2}{\overset{R_1}{\underset{|}{R-C-N}}}$$
$$\overset{O}{\|}$$

| Compound No. | R | R₁ | R₂ |
|---|---|---|---|
| 464 | " | —CHO | 3,4-dichlorophenyl-CH₂— |
| 465 | " | —CH₂—CH(CH₃)₂ | —CHCl₂ (with C=O) |
| 466 | " | H | —(CH₂)₃—O—CH(CH₃)₂ |
| 467 | " | " | 3,4-dichlorophenyl-CH₂— |
| 468 | " | " | —C(C₂H₅)(CH₃)₂ |
| 469 | " | " | —CH(CH₃)—phenyl |
| 470 | —CH₂Cl | " | —C(C₂H₅)(CH₃)₂ |
| 471 | " | " | —C₂H₄—O—CH₃ |
| 472 | " | " | —CH₂—CH(OCH₃)₂ |
| 473 | 3-fluorophenyl-CH=CH— | " | —C(CH₃)₂—C≡N |
| 474 | 4-methylphenyl-NH—C(=O)—CH₂Cl | " | —C(CH₃)₂—C≡CH |

TABLE I-continued $$\begin{array}{c} O \quad R_1 \\ \| \quad | \\ R-C-N \\ \quad\quad | \\ \quad\quad R_2 \end{array}$$

| Compound No. | R | $R_1$ | $R_2$ |
|---|---|---|---|
| 475 | —CHCl$_2$ | —CH$_2$—CH$_2$—O—C(=O)—N(CH$_3$)$_2$ | —CH$_2$—CH$_2$—O—C(=O)—N(CH$_3$)$_2$ |
| 476 | " | —CH$_2$—CH$_2$—O—C(=O)—NH—C$_2$H$_5$ | —CH$_2$—CH$_2$—O—C(=O)—NH—C$_2$H$_5$ |
| 477 | " | —CH$_2$—CH$_2$—O—C(=O)—NH—CH$_2$—CH=CH$_2$ | —CH$_2$—CH$_2$—O—C(=O)—NH—CH$_2$—CH=CH |
| 478 | " | —CH$_2$—CH$_2$—O—C(=O)—NH—i-C$_3$H$_7$ | —CH$_2$—CH$_2$—O—C(=O)—NH—i-C$_3$H$_7$ |
| 479 | " | —CH$_2$—CH$_2$—O—C(=O)—NH—C$_4$H$_9$ | —CH$_2$—CH$_2$—O—C(=O)—NH—C$_4$H$_9$ |
| 480 | —CH$_2$Cl | —CH$_2$—CH$_2$—O—C(=O)—NH—CH$_3$ | —CH$_2$—CH$_2$—O—C(=O)—NH—CH$_3$ |
| 481 | " | —CH$_2$—CH$_2$—O—C(=O)—NH—CH$_2$—CH=CH$_2$ | —CH$_2$—CH$_2$—O—C(=O)—NH—CH$_2$—CH=Cl |
| 482 | " | —CH$_2$—CH$_2$—O—C(=O)—NH—(tetrahydrothiopyranyl) | —CH$_2$—CH$_2$—O—C(=O)—NH—(tetrahydrothiopyranyl) |
| 483 | " | —CH$_2$—CH$_2$—O—C(=O)—NH—(3,4-dichlorophenyl) | —CH$_2$—CH$_2$—O—C(=O)—NH—(3,4-dichlorophenyl) |
| 484 | —CHCl$_2$ | H | —CH$_2$—CH$_2$—OH |
| 485 | —CH$_2$Cl | —CH$_2$—CH$_2$—OH | —CH$_2$—CH(OH)(CH$_3$) |
| 486 | —CHCl$_2$ | H | —(CH$_2$)$_3$—OH |
| 487 | " | " | —CH$_2$—CH(OH)(CH$_3$) |
| 488 | " | —CH$_2$—CH(OH)(CH$_3$) | —CH$_2$—CH(OH)(CH$_3$) |

TABLE I-continued $$\underset{R_1}{\overset{O}{\underset{\|}{R-C-N}}}\overset{R_2}{\underset{R_1}{}}$$

| Compound No. | R | $R_1$ | $R_2$ |
|---|---|---|---|
| 489 | " | | 2-methyl-2-tetrahydrofuryl (CH₃, CH₃ on oxolane) |
| 490 | —CH₂OH | —C₂H₅ | —C₂H₅ |
| 491 | —CH₃ | phenyl | phenyl-SO₂— |
| 492 | —CH₂—S—C₆H₄Cl (4-chlorophenylthiomethyl) | H | —CH₂—CH(CH₃)₂ |
| 493 | —CH₂—SO₂—O—CH₃ | —C₂H₅ | —C₂H₅ |
| 494 | —C₃H₆Br | H | —SO₂Cl |
| 495 | —CHCl₂ | 2,5-dimethylcyclohexyl | |
| 496 | —CCl₃ | —C₃H₇ | —C₃H₇ |
| 497 | " | | cyclohexyl |

TABLE I-continued
$$\underset{R_1}{\overset{O}{\underset{\|}{R-C-N}}}\overset{R_1}{\underset{R_2}{\diagdown}}$$
| Compound No. | R | $R_1$ | $R_2$ |
|---|---|---|---|
| 498 | " |  | |
| 499 | —CH₂Cl | —CH₃ | —CH₃ |
| 500 | —CCl₃ | H | —C₂H₄Br |
| 501 | —CH₂Cl | " | " |
| 502 | —CCl₃ | —C₂H₅ | —n-C₄H₉ |
| 503 | —CHCl₂ | —i-C₃H₇ | —i-C₃H₇ |
| 504 | " | —n-C₄H₉ | —n-C₄H₉ |
| 505 | " | —C₂H₅ | " |
| 506 | " | —i-C₃H₇ | —i-C₃H₇ |
| 507 | —CCl₃— | —i-C₄H₉ | —i-C₄H₉ |
| 508 | " | | |
| 509 | " | | |
| 510 | —CHCl₂ | H | ![2,6-diethylphenyl with CH₃] C₂H₅ / CH₃ / C₂H₅ |
| 511 | —CCl₃ | | —C(CH₃)(C₂H₅)—C≡N |
| 512 | —CH₂Cl | " | " |
| 513 | —CHCl₂ | " | " |

The compositions of this invention were tested in the following manner.

Test 1: Soil Incorporation

Small flats were filled with Felton loamy sand soil. The herbicide and herbicide antidote were applied separately or in combination to the soil as it is mixed in a five-gallon cement mixer. The following stock solutions were made up of each compound when the herbicide and antidote were applied separately. Stock solutions of the herbicide were diluted with 100 ml. of water. For the antidote, 700 mg. of technical material was diluted with 100 ml. of acetone. One ml. of these stock solutions is equivalent to 7 mg. active ingredient or one pound per acre when this treated soil was placed into 8×12×3" flats. After the soil was treated with the herbicide and the antidote at the desired rates, the soil was transferred from the cement mixer back into 8×12×3" flats where it was now ready for planting corn seed. A pint sample of soil was then remmoved from each flat and retained for covering the seeds after planting. The soil was leveled and rows one-half inch deep were made in each flat. Enough seeds were planted to obtain good stands in each treatment. Seeds were then covered up with the one pint of soil which had been removed just prior to planting.

The flats were then placed on greenhouse benches where temperatures were between 70°–90° F. The flats were watered by sprinkling as needed to assure good plant growth until rated. The crop tolerance was rated after three to six weeks. The results of these tests are set forth in Table II.

TABLE II

| Herbicide | Rate lb/A | Antidote Cmpd. No. | Rate lb/A | Crop | Injury to plants after 3 weeks % | 4 weeks % | 6 weeks % |
|---|---|---|---|---|---|---|---|
| EPTC | 6 | 6 | 1/16 | Corn | 0 | 0 | |
| EPTC | 6 | 6 | ⅛ | Corn | 0 | 0 | 0 |
| EPTC | 6 | 6 | ½ | Corn | 0 | 0 | 0 |
| EPTC | 6 | 6 | 1 | Corn | 0 | 0 | 0 |
| EPTC | 6 | 6 | 2 | Corn | 0 | 0 | 0 |
| EPTC | 6 | 6 | 5 | Corn | 0 | 0 | 0 |
| — | — | 6 | 5 | Corn | 0 | 0 | 0 |
| EPTC | 6 | 10 | ½ | Corn | 20 MF | | |
| EPTC | 6 | 11 | ½ | Corn | 0 | | |
| EPTC | 6 | 12 | ½ | Corn | 10 MF | | |
| EPTC | 6 | 13 | ½ | Corn | 60 MF | | |
| EPTC | 6 | 15 | ½ | Corn | 0 | | |
| EPTC | 6 | 16 | ½ | Corn | 10 MF | | |
| EPTC | 6 | 18 | ½ | Corn | 0 | | |
| EPTC | 6 | 8 | ½ | Corn | | 20 MF | |
| EPTC | 6 | 8 | 2 | Corn | | 0 | |
| EPTC | 6 | 7 | 2 | Corn | | 45 MF | |
| EPTC | 3 | 7 | 4 | Corn | 0 | | |
| EPTC | 6 | — | — | Corn | 94 MF | 97 MF | 98 MF |
| S—ethyl diisobutyl thiocarbamate | 8 | 7 | 2 | Corn | 15 MF | | |
| S—ethyl diisobutyl thiocarbamate | 8 | 7 | 4 | Corn | 0 | | |
| S—ethyl diisobutyl thiocarbamate | 8 | — | — | Corn | 75 MF | | |
| S—2,3,3-trichloro-allyl-diisopropyl thiolcarbamate | 1 | 6 | 4 | Wheat | 20 ST | | |
| S—2,3,3-Trichloro-allyl-diisopropyl thiolcarbamate | 1 | — | — | Wheat | 90 MF | | |
| EPTC + 2-chloro-4-ethyl-amino-6-isopropyl-amino-s-triazine | 6 + 1 | 6 | ½ | Corn | | 0 | |
| EPTC + 2-chloro-4-ethyl-amino-6-isopropyl-amino-s-triazine | 6 + 1 | 6 | 2 | Corn | | 0 | |
| EPTC + 2-chloro-4-ethyl-amino-6-isopropyl-amino-s-triazine | 6 + 1 | — | — | Corn | | 95 MF | |
| EPTC + 2-chloro-4,6-bis-(ethylamino)-s-triazine | 6 + 1 | 6 | ½ | Corn | | 0 | |
| EPTC + 2-chloro-4,6-bis-(ethylamino)-s-triazine | 6 + 1 | 6 | 2 | Corn | | 0 | |
| EPTC + 2-chloro-4,6-bis-(ethylamino)-s-triazine | 6 + 1 | — | — | Corn | | 90 MF | |
| EPTC + 2(4-chloro-6-ethyl-amino-s-triazine-2-yl-amino)-2- | 6 + 1 | 6 | ½ | Corn | | 0 | |

TABLE II-continued

| Herbicide | Rate lb/A | Antidote Cmpd. No. | Antidote Rate lb/A | Crop | Injury to plants after 3 weeks % | 4 weeks % | 6 weeks % |
|---|---|---|---|---|---|---|---|
| methylpropionitrile EPTC + 2(4-chloro-6-ethyl-amino-s-triazine-2-yl-amino)-2-methylpropionitrile | 6 + 1 | — | — | Corn | | 80 MF | |
| EPTC + 2-chloro-4-cyclo-propylamino-6-isopropylamino-s-triazine | 6 + 1 | 6 | ⅛ | Corn | | 0 | |
| EPTC + 2-chloro-4-cyclo-propylamino-6-isopropylamino-s-triazine | 6 + 1 | — | — | Corn | | 90 MF,ST | |
| EPTC + 2,4-D | 6 + 1 | 6 | ⅛ | Corn | | 0 | |
| EPTC + 2,4-D | 6 + 1 | 6 | 2 | Corn | | 10 ST | |
| EPTC + 2,4-D | 6 + 1 | — | — | Corn | | 50 MF | |
| S—propyl dipropyl thiolcarbamate + 2-chloro-4-ethyl-amino-6-isopropyl-amino-s-triazine | 6 + 1 | 6 | ⅛ | Corn | | 3 MF | |
| S—propyl dipropyl thiolcarbamate + 2-chloro-4-ethyl-amino-6-isopropyl-amino-s-triazine | 6 + 1 | 6 | 2 | Corn | | 0 | |
| S—propyl dipropyl thiolcarbamate + 2-chloro-4-ethyl-amino-6-isopropyl-amino-s-triazine | 6 + 2 | 6 | ⅛ | Corn | | 0 | |
| S—propyl dipropyl thiolcarbamate + 2-chloro-4-ethyl-amino-6-isopropyl-amino-s-triazine | 3 + 1 | 6 | ⅛ | Corn | | 0 | |
| S—propyl dipropyl thiolcarbamate + 2-chloro-4-ethyl-amino-6-isopropyl-amino-s-triazine | 3 + 1 | — | — | Corn | | 70 MF | |
| S—propyl dipropyl thiolcarbamate + 2-chloro-4-ethyl-amino-6-isopropyl-amino-s-triazine | 6 + 1 | — | — | Corn | | 90 MF | |
| S—propyl dipropyl thiolcarbamate 2-chloro-4,6-bis-(ethylamino)-s-triazine | 6 + 1 | 6 | ⅛ | Corn | | 3 MF | |
| S—propyl dipropyl thiolcarbamate + 2-chloro-4,6-bis-(ethylamino)-s-triazine | 6 + 1 | 6 | 2 | Corn | | 0 | |
| S—propyl dipropyl thiolcarbamate + 2-chloro-4,6-bis-(ethylamino)-s-triazine | 6 + 1 | — | — | Corn | | 70 MF | |
| S—propyl dipropyl thiolcarbamate + 2(4-chloro-6-ethyl-amino-s-triazine-2-yl-amino)-2-methylpropionitrile | 6 + 1 | 6 | ⅛ | Corn | | 0 | |
| S—propyl dipropyl thiolcarbamate + 2(4-chloro-6-ethyl-amino-s-triazine-2-yl-amino)-2-methyl-propionitrile | 6 + 1 | — | — | Corn | | 97 MF | |

TABLE II-continued

| Herbicide | Rate lb/A | Antidote Cmpd. No. | Rate lb/A | Crop | Injury to plants after 3 weeks % | 4 weeks % | 6 weeks % |
|---|---|---|---|---|---|---|---|
| S—propyl dipropyl thiolcarbamate + 2-chloro-4-cyclo-propylamino-6-iso-propylamino-s-triazine | 6 + 1 | 6 | 1/8 | Corn | | 0 | |
| S—propyl dipropyl thiolcarbamate + 2-chloro-4-cyclo-propylamino-6-iso-propylamino-s-triazine | 6 + 1 | — | — | Corn | | 92 MF | |
| S—propyl dipropyl thiolcarbamate + 2,4-D | 6 + 1 | 6 | 1/8 | Corn | | 0 | |
| S—propyl dipropyl thiolcarbamate + 2,4-D | 6 + 1 | 6 | 2 | Corn | | 0 | |
| S—propyl dipropyl thiolcarbamate + 2,4-D | 6 + 1 | — | — | Corn | | 60 ST,MF | |
| S—propyl dipropyl thiolcarbamate | 6 | 6 | 1/8 | Corn | | 0 | |
| S—propyl dipropyl thiolcarbamate | 6 | 6 | 2 | Corn | | 0 | |
| S—propyl dipropyl thiolcarbamate | 6 | — | — | Corn | | 90 MF | |
| S—ethyl diisobutyl-thiolcarbamate + 2-chloro-4-ethyl-amino-6-isopropyl-amino-s-triazine | 8 + 1 | 6 | 1/8 | Corn | | 0 | |
| S—ethyl diisobutyl-thiolcarbamate + 2-chloro-4-ethyl-amino-6-isopropyl-amino-s-triazine | 8 + 1 | 6 | 2 | Corn | | 0 | |
| S—ethyl diisobutyl thiolcarbamate + 2-chloro-4-ethyl-amino-6-isopropyl-amino-s-triazine | 8 + 1 | — | — | Corn | | 0 | |
| S—ethyl diisobutyl-thiolcarbamate + 2-chloro-4,6-bis-(ethylamino)-s-triazine | 8 + 1 | 6 | 1/8 | Corn | | 0 | |
| S—ethyl diisobutyl-thiolcarbamate + 2-chloro-4,6-bis-(ethylamino)-s-triazine | 8 + 1 | 6 | 2 | Corn | | 0 | |
| S—ethyl diisobutyl-thiolcarbamate + 2-chloro-4,6-bis-(ethylamino)-s-triazine | 8 + 1 | — | — | Corn | | 0 | |
| S—ethyl diisobutyl-thiolcarbamate + 2(4-chloro-6-ethyl-amino-s-triazine-2-yl-amino)-2-methylpropionitrile | 8 + 1 | 6 | 1/8 | Corn | | 0 | |
| S—ethyl diisobutyl-thiolcarbamate + 2(4-chloro-6-ethyl-amino-s-triazine-2-yl-amino)-2-methylpropionitrile | 8 + 1 | — | — | Corn | | 20 MF | |
| S—ethyl diisobutyl-thiolcarbamate + 2-chloro-4-cyclo-propylamino-6-iso-propylamino-s-triazine | 8 + 1 | 6 | 1/8 | Corn | | 0 | |
| S—ethyl diisobutyl-thiolcarbamate + 2-chloro-4-cyclo-propylamino-6-iso- | 8 + 1 | — | — | Corn | | 10 MF | |

TABLE II-continued

| Herbicide | Rate lb/A | Antidote Cmpd. No. | Antidote Rate lb/A | Crop | Injury to plants after 3 weeks % | 4 weeks % | 6 weeks % |
|---|---|---|---|---|---|---|---|
| propylamino-s-triazine | | | | | | | |
| S—ethyl diisobutyl-thiolcarbamate + 2,4-D | 8 + 1 | 6 | ½ | Corn | | 0 | |
| S—ethyl diisobutyl-thiolcarbamate + 2,4-D | 8 + 1 | 6 | 2 | Corn | | 0 | |
| S—ethyl diisobutyl-thiolcarbamate + 2,4-D | 8 + 1 | — | — | Corn | | 0 | |
| S—ethyl diisobutyl-thiolcarbamate | 8 | 6 | ½ | Corn | | 0 | |
| S—ethyl diisobutyl-thiolcarbamate | 8 | 6 | 2 | Corn | | 0 | |
| S—ethyl diisobutyl-thiolcarbamate | 8 | — | — | Corn | | 20 ST | |
| S—2,3,3-trichloro-allyl-diisopropyl-thiolcarbamate | 8 | 6 | ½ | Corn | | 10 ST | |
| S—2,3,3-trichloro-allyl-diisopropyl-thiolcarbamate | 8 | — | — | Corn | | 30 ST | |
| S—2,3,3-trichloro-allyl-diisopropyl-thiolcarbamate | 3 | 6 | 5 | Wheat | | 70 | |
| S—2,3,3-trichloro-allyl-diisopropyl-thiolcarbamate | 3 | — | — | Wheat | | 95 | |
| S—2,3,3-trichloro-allyl-diisopropyl-thiolcarbamate | 3 | 6 | 5 | Milo | | 10 | |
| S—2,3,3-trichloro-allyl-diisopropyl-thiolcarbamate | 3 | — | — | Milo | | 90 | |
| 2-chloro-2',6'-diethyl-N—(methoxy-methyl) acetanilide | 3 | 6 | 5 | Milo | | 20 | |
| 2-chloro-2',6'-diethyl-N—(methoxy-methyl) acetanilide | 3 | — | — | Milo | | 70 | |
| S—ethyl hexahydro-1H—azepine-1-carbothioate | 3 | 6 | 5 | Rice | | 0 | |
| S—ethyl hexahydro-1H—azepine-1-carbothioate | 3 | — | — | Rice | | 20 | |
| 2-chloro-N—iso-propylacetanilide | 3 | 6 | 5 | Wheat | | 20 | |
| 2-chloro-N—iso-propylacetanilide | 3 | — | — | Wheat | | 40 | |
| N,N—diallyl-2-chloroacetamide | 4 | 6 | 5 | Milo | | 20 | |
| N,N—diallyl-2-chloroacetamide | 4 | — | — | Milo | | 70 | |
| S—4-chlorobenzyl diethyl thiolcarbamate | 6 | — | — | Rice | | 50 | |
| S—4-chlorobenzyl diethyl thiolcarbamate | 6 | 6 | 5 | Rice | | 30 | |
| S—4-chlorobenzyl diethyl thiolcarbamate | 12 | — | — | Rice | | 90 | |
| S—4-chlorobenzyl diethyl thiolcarbamate | 12 | 6 | 5 | Rice | | 30 | |
| S—4-chlorobenzyl diethyl thiolcarbamate | 12 | — | — | Corn | | 40 | |
| S—4-chlorobenzyl diethyl thiolcarbamate | 12 | 6 | 5 | Corn | | 0 | |
| S—ethyl cyclohexyl ethyl thiocarbamate | 6 | 6 | 0.1 | Corn | | 50 MF | |
| S—ethyl cyclohexyl | 6 | — | — | Corn | | 80 MF | |

TABLE II-continued

| Herbicide | Rate lb/A | Antidote Cmpd. No. | Rate lb/A | Crop | Injury to plants after 3 weeks % | 4 weeks % | 6 weeks % |
|---|---|---|---|---|---|---|---|
| ethyl thiocarbamate | | | | | | | |

EPTC = S—ethyl, dipropylthiocarbamate
ST = stunting
MF = malformation

Test 2: Corn Seed Treatment

Small flats were filled with Felton loamy sand soil. Soil incorporated herbicides were applied at this time. The soil from each flat was placed into a five-gallon cement mixer where the soil was mixed as the herbicides were applied as a stock solution in 100 ml. of water. One ml. of stock solution was applied to the soil in a volumetric pipet for each pound of herbicide desired. One ml. of stock solution contains seven mg of herbicide which equals one pound per acre when applied to soil in 8×12×3" flats. After the herbicide incorporation, the soil was placed back into the flats.

Flats of herbicide-treated and untreated soil were then ready to be planted. A pint sample of soil was then removed from each flat and placed next to each flat for later use in covering up the seeds. The soil was leveled and rows one-half inches deep were made for planting seeds. Alternating rows of treated and untreated crop seeds were sown. In each test six or more seeds were planted in each row. Rows were approximately 1-½" apart in the flat. Seed treatment was applied by placing 50 mg. of the seed treatment compound with 10 grams of seed in a suitable container and shaking them until the seeds were uniformly covered with the seed treatment. Seed treatment compounds were applied as liquid slurries and powder or dust treatments. In some cases acetone was used to dissolve powdered or solid compounds so they could be more effectively applied to the seeds.

After flats were seeded they were covered with the one pint of soil which had been removed just prior to planting. Flats were placed on greenhouse benches where temperatures ranged from 70°–90° C. Flats were watered by sprinkling as needed to assure good plant growth. Percent injury ratings were taken two to four weeks after treatments were applied.

In each test, the herbicide is applied alone, in combination with the seed protectant and the seed protectant is applied alone to check for phytotoxicity. The results of these tests are tabulated in Table III.

TABLE III

| Herbicide | Rate lb/A | Antidote Cmpd. No. | Treatment Rate % w/w | Crop | % Injury Treated Seed 2 weeks | 4 weeks | Untreated Seed in Adjacent Row 2 weeks | 4 weeks |
|---|---|---|---|---|---|---|---|---|
| EPTC | 6 | 1 | .5 | Corn | 20 MF | 60 ST,MF | | |
| EPTC | 6 | 2 | .5 | Corn | 10 ST | 40 ST,MF | | |
| EPTC | 6 | 3 | .5 | Corn | 0 | 60 ST,MF | | |
| EPTC | 6 | 4 | .5 | Corn | 10 ST | 70 ST,MF | | |
| EPTC | 6 | 5 | .5 | Corn | 0 | 30 ST,MF | | |
| EPTC | 6 | 6 | .5 | Corn | 0 | 0 | 0 | 0 |
| EPTC | 6 | 7 | .5 | Corn | | 30 ST | | |
| EPTC | 6 | 8 | .05 | Corn | | 0 | | |
| EPTC | 6 | 9 | .5 | Corn | 10 ST | | 30 MF | |
| EPTC | 6 | 10 | .5 | Corn | 10 ST | | 5 MF | |
| EPTC | 6 | 11 | .5 | Corn | 10 ST | | 10 MF | |
| EPTC | 6 | 12 | .5 | Corn | 100 IG | | 5 MF | |
| EPTC | 6 | 13 | .5 | Corn | 100 IG | | 15 MF | |
| EPTC | 6 | 14 | .5 | Corn | 10 ST | | 50 MF | |
| EPTC | 6 | 15 | .5 | Corn | 100 IG | | 5 ST | |
| EPTC | 6 | 16 | .5 | Corn | 10 ST | | 5 ST | |
| EPTC | 6 | 17 | .5 | Corn | 20 ST | | 35 MF | |
| EPTC | 6 | 18 | .5 | Corn | 0 | | 5 ST | |
| EPTC | 6 | 19 | .5 | Corn | 0 | | 50 MF | |
| EPTC | 6 | 20 | .5 | Corn | 10 ST | 10 ST | 30 MF | 65 MF |
| EPTC | 6 | 21 | .5 | Corn | 0 | 0 | 10 MF | 55 MF |
| EPTC | 6 | 22 | .5 | Corn | 60 MF | 70 MF | 85 MF | 80 MF |
| EPTC | 6 | 23 | .5 | Corn | 20 MF | 40 MF | 85 MF | 80 MF |
| EPTC | 6 | 24 | .5 | Corn | 10 ST | 10 ST | 75 MF | 80 MF |
| EPTC | 6 | 25 | .5 | Corn | 0 | 30 MF | 60 MF | 60 MF |
| EPTC | 6 | 26 | .5 | Corn | 0 | 10 MF | 83 MF | 80 MF |
| EPTC | 6 | 27 | .5 | Corn | 70 MF | | 60 MF | |
| EPTC | 6 | 28 | .5 | Corn | 30 ST,MF | | 75 MF | |
| EPTC | 6 | 29 | .5 | Corn | 60 MF | | 70 MF | |
| EPTC | 6 | 30 | .5 | Corn | 60 MF | | 70 MF | |
| EPTC | 6 | 31 | .5 | Corn | 70 MF | | 80 MF | |
| EPTC | 6 | 32 | .5 | Corn | 60 MF | | 75 MF | |
| EPTC | 6 | 33 | .5 | Corn | 50 ST,MF | | 75 MF | |
| EPTC | 6 | 34 | .5 | Corn | 60 MF | | 80 MF | |
| EPTC | 6 | 35 | .5 | Corn | 50 MF | | 75 MF | |
| EPTC | 6 | 36 | .5 | Corn | 60 MF | | 85 MF | |
| EPTC | 6 | 37 | .5 | Corn | 40 ST,MF | | 85 MF | |
| EPTC | 6 | 38 | .5 | Corn | 60 MF | | 80 MF | |
| EPTC | 6 | 39 | .5 | Corn | 60 MF | | 70 MF | |
| EPTC | 6 | 40 | .5 | Corn | 50 MF | | 80 MF | |
| EPTC | 6 | 41 | .5 | Corn | 10 ST,MF | 50 MF | 75 MF | 65 MF |

TABLE III-continued

| | | Antidote | | | % Injury | | | |
| | | | | | Treated Seed | | Untreated Seed in Adjacent Row | |
| Herbicide | Rate lb/A | Cmpd. No. | Treatment Rate % w/w | Crop | 2 weeks | 4 weeks | 2 weeks | 4 weeks |
|---|---|---|---|---|---|---|---|---|
| EPTC | 6 | 42 | .5 | Corn | 60 MF | | 80 MF | |
| EPTC | 6 | 43 | .5 | Corn | 10 ST,MF | 50 MF | 85 MF | 80 MF |
| EPTC | 6 | 44 | .5 | Corn | 40 MF | | 70 MF | |
| EPTC | 6 | 45 | .5 | Corn | 60 MF | | 85 MF | |
| EPTC | 6 | 46 | .5 | Corn | 40 ST,MF | | 85 MF | |
| EPTC | 6 | 47 | .5 | Corn | 60 MF | | 80 MF | |
| EPTC | 6 | 48 | .5 | Corn | 50 ST,MF | | 80 MF | |
| EPTC | 6 | 49 | .5 | Corn | 60 MF | | 70 MF | |
| EPTC | 6 | 50 | .5 | Corn | 60 MF | | 90 MF | |
| EPTC | 6 | 51 | .5 | Corn | 60 MF | | 70 MF | |
| EPTC | 6 | 52 | .5 | Corn | 60 ST,MF | | 80 MF | |
| EPTC | 6 | 53 | .5 | Corn | 50 MF | | 70 MF | |
| EPTC | 6 | 54 | .5 | Corn | 60 MF | | 70 MF | |
| EPTC | 6 | 55 | .5 | Corn | 60 MF | | 80 MF | |
| EPTC | 6 | 56 | .5 | Corn | 60 MF | | 80 MF | |
| EPTC | 6 | 57 | .5 | Corn | 60 MF | | 65 MF | |
| EPTC | 6 | 58 | .5 | Corn | 50 MF | | 75 MF | |
| EPTC | 6 | 59 | .5 | Corn | 60 ST,MF | | 80 MF | |
| EPTC | 6 | 60 | .5 | Corn | 60 ST,MF | | 75 MF | |
| EPTC | 6 | 61 | .5 | Corn | 60 MF | | 85 MF | |
| EPTC | 6 | 62 | .5 | Corn | 40 ST,MF | 60 MF | 80 MF | 70 MF |
| EPTC | 6 | 63 | .5 | Corn | 30 ST,MF | 60 MF | 70 MF | 70 MF |
| EPTC | 6 | 64 | .5 | Corn | 30 ST,MF | 50 MF | 65 MF | 70 MF |
| EPTC | 6 | 65 | .5 | Corn | 60 ST,MF | 70 MF | 75 MF | 80 MF |
| EPTC | 6 | 66 | .5 | Corn | 50 ST,MF | | 70 MF | |
| EPTC | 6 | 67 | .5 | Corn | 40 ST,MF | | 80 MF | |
| EPTC | 6 | 68 | .5 | Corn | 60 MF | 50 MF | 80 MF | 70 MF |
| EPTC | 6 | 69 | .5 | Corn | 20 ST,MF | 50 ST,MF | 70 MF | 80 MF |
| EPTC | 6 | 70 | .5 | Corn | 40 ST,MF | | 80 MF | |
| EPTC | 6 | 71 | .5 | Corn | 40 ST,MF | | 80 MF | |
| EPTC | 6 | 72 | .5 | Corn | 60 MF | | 65 MF | |
| EPTC | 6 | 73 | .5 | Corn | 60 MF | | 80 MF | |
| EPTC | 6 | 74 | .5 | Corn | 60 MF | | 80 MF | |
| EPTC | 6 | 75 | .5 | Corn | 60 ST,MF | | 80 MF | |
| EPTC | 6 | 76 | .5 | Corn | 50 ST,MF | | 75 MF | |
| EPTC | 6 | 77 | .5 | Corn | 60 MF | | 75 MF | |
| EPTC | 6 | 78 | .5 | Corn | 60 ST,MF | | 75 MF | |
| EPTC | 6 | 79 | .5 | Corn | 50 ST,MF | | 75 MF | |
| EPTC | 6 | 80 | .5 | Corn | 60 MF | 60 MF | 65 MF | 70 MF |
| EPTC | 6 | 81 | .5 | Corn | 10 ST | 20 MF | 50 MF | 50 MF |
| EPTC | 6 | 82 | .5 | Corn | 30 ST | 30 ST | 50 MF | 50 MF |
| EPTC | 6 | 83 | .5 | Corn | 20 ST | 20 ST | 20 MF | 25 MF |
| EPTC | 6 | 84 | .5 | Corn | 10 ST | 10 ST | 15 MF | 20 MF |
| EPTC | 6 | 85 | .5 | Corn | 30 ST | 10 ST | 35 MF | 45 MF |
| EPTC | 6 | 86 | .5 | Corn | 50 ST,MF | | 75 MF | |
| EPTC | 6 | 87 | .5 | Corn | 30 ST,MF | | 75 MF | |
| EPTC | 6 | 88 | .5 | Corn | 50 ST,MF | | 70 MF | |
| EPTC | 6 | 89 | .5 | Corn | 60 MF | | 80 MF | |
| EPTC | 6 | 90 | .5 | Corn | 20 ST,MF | 30 ST,MF | 80 MF | 80 MF |
| EPTC | 6 | 91 | .5 | Corn | 40 ST,MF | | 80 MF | |
| EPTC | 6 | 92 | .5 | Corn | 50 ST,MF | | 80 MF | |
| EPTC | 6 | 93 | .5 | Corn | 60 ST | 20 ST | 75 MF | 75 MF |
| EPTC | 6 | 94 | .5 | Corn | 30 ST,MF | | 80 MF | |
| EPTC | 6 | 95 | .5 | Corn | 100 IG | | 90 MF | |
| EPTC | 6 | 96 | .5 | Corn | 30 ST,MF | | 80 MF | |
| EPTC | 6 | 97 | .5 | Corn | 30 ST,MF | | 75 MF | |
| EPTC | 6 | 98 | .5 | Corn | 60 ST,MF | | 75 MF | |
| EPTC | 6 | 99 | .5 | Corn | 30 ST | 30 ST,MF | 85 MF | 80 MF |
| EPTC | 6 | 100 | .5 | Corn | 40 ST,MF | | 65 MF | |
| EPTC | 6 | 101 | .5 | Corn | 50 ST,MF | | 75 MF | |
| EPTC | 6 | 102 | .5 | Corn | 30 ST,MF | 50 MF | 85 MF | 80 MF |
| EPTC | 6 | 103 | .5 | Corn | 50 MF | | 80 MF | |
| EPTC | 6 | 104 | .5 | Corn | 40 ST,MF | | 85 MF | |
| EPTC | 6 | 105 | .5 | Corn | 50 ST,MF | | 85 MF | |
| EPTC | 6 | 106 | .5 | Corn | 40 ST,MF | | 80 MF | |
| EPTC | 6 | 107 | .5 | Corn | 30 ST | 20 ST,MF | 85 MF | 80 MF |
| EPTC | 6 | 108 | .5 | Corn | 40 ST,MF | | 90 MF | |
| EPTC | 6 | 109 | .5 | Corn | 30 ST,MF | | 90 MF | |
| EPTC | 6 | 110 | .5 | Corn | 40 ST,MF | | 85 MF | |
| EPTC | 6 | 111 | .5 | Corn | 40 ST,MF | | 75 MF | |
| EPTC | 6 | 112 | .5 | Corn | 60 ST,IG | 30 MF | 85 MF | 80 MF |
| EPTC | 6 | 113 | .5 | Corn | 30 ST,MF | | 80 MF | |
| EPTC | 6 | 114 | .5 | Corn | 30 ST,MF | | 80 MF | |
| EPTC | 6 | 115 | .5 | Corn | 40 ST,MF | | 90 MF | |
| EPTC | 6 | 116 | .5 | Corn | 30 ST | 30 ST,MF | 75 MF | 80 MF |
| EPTC | 6 | 117 | .5 | Corn | 20 ST,MF | | 70 MF | |
| EPTC | 6 | 118 | .5 | Corn | 30 ST,MF | | 70 MF | |

TABLE III-continued

| | | Antidote | | | % Injury | | | |
| | | | | | Treated Seed | | Untreated Seed in Adjacent Row | |
| Herbicide | Rate lb/A | Cmpd. No. | Treatment Rate % w/w | Crop | 2 weeks | 4 weeks | 2 weeks | 4 weeks |
|---|---|---|---|---|---|---|---|---|
| EPTC | 6 | 119 | .5 | Corn | 30 ST,MF | | 70 MF | |
| EPTC | 6 | 120 | .5 | Corn | 30 ST,MF | | 75 MF | |
| EPTC | 6 | 121 | .5 | Corn | 40 ST,MF | | 75 MF | |
| EPTC | 6 | 122 | .5 | Corn | 20 ST,MF | | 35 MF | |
| EPTC | 6 | 123 | .5 | Corn | 20 ST | 20 ST | 10 MF | 20 MF |
| EPTC | 6 | 124 | .5 | Corn | 30 ST,MF | | 75 MF | |
| EPTC | 6 | 125 | .5 | Corn | 40 ST,MF | | 80 MF | |
| EPTC | 6 | 126 | .5 | Corn | 40 ST,MF | | 80 MF | |
| EPTC | 6 | 127 | .5 | Corn | 60 MF | | 80 MF | |
| EPTC | 6 | 128 | .5 | Corn | 50 MF | | 55 MF | |
| EPTC | 6 | 129 | .5 | Corn | 30 ST,LB | 30 ST,LB | 50 MF | 60 MF |
| EPTC | 6 | 130 | .5 | Corn | 30 ST | 30 ST | 40 MF | 60 MF |
| EPTC | 6 | 131 | .5 | Corn | 10 ST | 0 | 25 MF | 55 MF |
| EPTC | 6 | 132 | .5 | Corn | 0 | 0 | 45 MF | 55 MF |
| EPTC | 6 | 133 | .5 | Corn | 40 MF | | 65 MF | |
| EPTC | 6 | 134 | .5 | Corn | 30 ST,MF | | 70 MF | |
| EPTC | 6 | 135 | .5 | Corn | 40 ST,MF | | 70 MF | |
| EPTC | 6 | 136 | .5 | Corn | 50 ST,MF | | 80 MF | |
| EPTC | 6 | 137 | .5 | Corn | 30 ST,MF | | 85 MF | |
| EPTC | 6 | 138 | .5 | Corn | 30 ST,MF | | 75 MF | |
| EPTC | 6 | 139 | .5 | Corn | 50 ST,MF | | 80 MF | |
| EPTC | 6 | 140 | .5 | Corn | 50 ST,MF | | 75 MF | |
| EPTC | 6 | 141 | .5 | Corn | 20 ST,MF | 30 ST,MF | 80 MF | 80 MF |
| EPTC | 6 | 142 | .5 | Corn | 20 ST,MF | 50 MF | 75 MF | 70 MF |
| EPTC | 6 | 143 | .5 | Corn | 10 ST,MF | 50 MF | 85 MF | 80 MF |
| EPTC | 6 | 144 | .5 | Corn | 50 ST,MF | | 85 MF | |
| EPTC | 6 | 145 | .5 | Corn | 20 ST,MF | | 80 MF | |
| EPTC | 6 | 146 | .5 | Corn | 20 ST,MF | 20 ST,MF | 65 MF | 70 MF |
| EPTC | 6 | 147 | .5 | Corn | 10 ST | 0 | 75 MF | 80 MF |
| EPTC | 6 | 148 | .5 | Corn | 60 MF | | 75 MF | |
| EPTC | 6 | 149 | .5 | Corn | 40 ST,MF | | 75 MF | |
| EPTC | 6 | 150 | .5 | Corn | 50 ST,MF | | 70 MF | |
| EPTC | 6 | 151 | .5 | Corn | 50 MF | | 70 MF | |
| EPTC | 6 | 152 | .5 | Corn | 40 MF | | 80 MF | |
| EPTC | 6 | 153 | .5 | Corn | 50 MF | | 85 MF | |
| EPTC | 6 | 154 | .5 | Corn | 30 ST,MF | | 75 MF | |
| EPTC | 6 | 155 | .5 | Corn | 20 ST,MF | 40 MF | 85 MF | 80 MF |
| EPTC | 6 | 156 | .5 | Corn | 60 MF | | 85 MF | |
| EPTC | 6 | 157 | .5 | Corn | 50 ST,MF | | 80 MF | |
| EPTC | 6 | 158 | .5 | Corn | 20 ST,MF | | 70 MF | |
| EPTC | 6 | 159 | .5 | Corn | 30 ST,MF | | 75 MF | |
| EPTC | 6 | 160 | .5 | Corn | 50 ST,MF | | 75 MF | |
| EPTC | 6 | 161 | .5 | Corn | 50 ST,MF | | 70 MF | |
| EPTC | 6 | 162 | .5 | Corn | 30 ST,MF | | 65 MF | |
| EPTC | 6 | 163 | .5 | Corn | 60 ST,MF | | 60 MF | |
| EPTC | 6 | 164 | .5 | Corn | 60 MF | | 70 MF | |
| EPTC | 6 | 165 | .5 | Corn | 60 MF | | 75 MF | |
| EPTC | 6 | 166 | .5 | Corn | 40 ST,MF | 60 MF | 75 MF | 60 MF |
| EPTC | 6 | 167 | .5 | Corn | 50 ST,MF | | 75 MF | |
| EPTC | 6 | 168 | .5 | Corn | 60 ST,MF | | 80 MF | |
| EPTC | 6 | 169 | .5 | Corn | 30 ST | 30 ST | 80 MF | 80 MF |
| EPTC | 6 | 170 | .5 | Corn | 30 ST,MF | | 80 MF | |
| EPTC | 6 | 171 | .5 | Corn | 60 MF | | 75 MF | |
| EPTC | 6 | 172 | .5 | Corn | 40 MF | | 75 MF | |
| EPTC | 6 | 173 | .5 | Corn | 30 ST,MF | 50 MF | 80 MF | 80 MF |
| EPTC | 6 | 174 | .5 | Corn | 60 ST,MF | | 80 MF | |
| EPTC | 6 | 175 | .5 | Corn | 30 ST,MF | | 85 MF | |
| EPTC | 6 | 176 | .5 | Corn | 40 ST,MF | | 85 MF | |
| EPTC | 6 | 177 | .5 | Corn | 30 ST,MF | | 85 MF | |
| EPTC | 6 | 178 | .5 | Corn | 50 ST,MF | | 80 MF | |
| EPTC | 6 | 179 | .5 | Corn | 0 | 0 | 0 | 5 MF |
| EPTC | 6 | 180 | .5 | Corn | 0 | 0 | 0 | 0 |
| EPTC | 6 | 181 | .5 | Corn | 0 | 0 | 0 | 0 |
| EPTC | 6 | 182 | .5 | Corn | 0 | 0 | 0 | 0 |
| EPTC | 6 | 183 | .5 | Corn | 0 | 0 | 0 | 0 |
| EPTC | 6 | 184 | .5 | Corn | 0 | 0 | 5 MF | 15 MF |
| EPTC | 6 | 185 | .5 | Corn | 0 | 0 | 3 MF | 30 MF |
| EPTC | 6 | 186 | .5 | Corn | 0 | 0 | 0 | 0 |
| EPTC | 6 | 187 | .5 | Corn | 0 | 0 | 5 MF | 45 MF |
| EPTC | 6 | 188 | .5 | Corn | 0 | 0 | 13 MF | 45 MF |
| EPTC | 6 | 189 | .5 | Corn | 0 | 0 | 5 MF | 35 MF |
| EPTC | 6 | 190 | .5 | Corn | 0 | 0 | 0 | 15 MF |
| EPTC | 6 | 191 | .5 | Corn | 0 | 0 | 3 MF | 50 MF |
| EPTC | 6 | 192 | .5 | Corn | 0 | 0 | 5 MF | 40 MF |
| EPTC | 6 | 193 | .5 | Corn | 0 | 0 | 10 MF | 35 MF |
| EPTC | 6 | 194 | .5 | Corn | 0 | 0 | 0 | 25 MF |
| EPTC | 6 | 195 | .5 | Corn | 30 ST,MF | | 55 MF | |

TABLE III-continued

| Herbicide | Rate lb/A | Antidote Cmpd. No. | Treatment Rate % w/w | Crop | % Injury Treated Seed 2 weeks | 4 weeks | Untreated Seed in Adjacent Row 2 weeks | 4 weeks |
|---|---|---|---|---|---|---|---|---|
| EPTC | 6 | 196 | .5 | Corn | 100 IG | | 55 MF | |
| EPTC | 6 | 197 | .5 | Corn | 60 MF | | 75 MF | |
| EPTC | 6 | 198 | .5 | Corn | 30 ST,MF | 30 MF | 75 MF | 80 MF |
| EPTC | 6 | 199 | .5 | Corn | 50 ST,MF | | 80 MF | |
| EPTC | 6 | 200 | .5 | Corn | 60 MF | | 80 MF | |
| EPTC | 6 | 201 | .5 | Corn | 40 ST,MF | | 88 MF | |
| EPTC | 6 | 202 | .5 | Corn | 50 MF | | 60 MF | |
| EPTC | 6 | 203 | .5 | Corn | 50 MF | | 65 MF | |
| EPTC | 6 | 204 | .5 | Corn | 20 ST | 10 ST | 55 MF | 50 MF |
| EPTC | 6 | 205 | .5 | Corn | 30 ST,MF | | 65 MF | |
| EPTC | 6 | 206 | .5 | Corn | 20 ST,MF | 20 ST,MF | 40 MF | 55 MF |
| EPTC | 6 | 207 | .5 | Corn | 100 IG | | 55 MF | |
| EPTC | 6 | 208 | .5 | Corn | 60 ST,MF | | 70 MF | |
| EPTC | 6 | 209 | .5 | Corn | 0 | 0 | 30 MF | 40 MF |
| EPTC | 6 | 210 | .5 | Corn | 0 | 10 ST | 5 MF | 35 MF |
| EPTC | 6 | 211 | .5 | Corn | 0 | 0 | 25 MF | 50 MF |
| EPTC | 6 | 212 | .5 | Corn | 0 | 10 ST | 18 MF | 50 MF |
| EPTC | 6 | 213 | .5 | Corn | 50 ST | 30 ST | 70 MF | 70 MF |
| EPTC | 6 | 214 | .5 | Corn | 0 | 10 ST | 50 MF | 65 MF |
| EPTC | 6 | 215 | .5 | Corn | 10 ST | 0 | 85 MF | 70 MF |
| EPTC | 6 | 216 | .5 | Corn | 10 ST | 10 ST,MF | 95 MF | 90 MF |
| EPTC | 6 | 217 | .5 | Corn | 100 IG | 100 IG | 30 MF | 45 MF |
| EPTC | 6 | 218 | .5 | Corn | 10 ST | 10 ST | 20 MF | 15 MF |
| EPTC | 6 | 219 | .5 | Corn | 100 IG | | 45 MF | |
| EPTC | 6 | 220 | .5 | Corn | 0 | 10 ST | 0 | 0 |
| EPTC | 6 | 221 | .5 | Corn | 0 | 10 ST | 15 MF | 35 MF |
| EPTC | 6 | 222 | .5 | Corn | 100 IG | | 50 MF | |
| EPTC | 6 | 223 | .5 | Corn | 10 ST | 20 ST | 70 MF | 70 MF |
| EPTC | 6 | 224 | .5 | Corn | 50 ST | 30 ST | 45 MF | 80 MF |
| EPTC | 6 | 225 | .5 | Corn | 30 ST | 30 ST | 70 MF | 80 MF |
| EPTC | 6 | 226 | .5 | Corn | 20 ST | 10 ST | 93 MF | 80 MF |
| EPTC | 6 | 227 | .5 | Corn | 20 ST | 20 ST | 85 MF | 80 MF |
| EPTC | 6 | 228 | .5 | Corn | 40 ST,MF | | 93 MF | |
| EPTC | 6 | 229 | .5 | Corn | 40 ST,MF | | 90 MF | |
| EPTC | 6 | 230 | .5 | Corn | 40 ST,MF | | 95 MF | |
| EPTC | 6 | 231 | .5 | Corn | 40 ST,MF | | 88 MF | |
| EPTC | 6 | 232 | .5 | Corn | 0 | 0 | 55 MF | 60 MF |
| EPTC | 6 | 233 | .5 | Corn | 30 ST,MF | | 70 MF | |
| EPTC | 6 | 234 | .5 | Corn | 0 | 10 ST | 55 MF | 60 MF |
| EPTC | 6 | 235 | .5 | Corn | 10 ST | 10 ST | 70 MF | 65 MF |
| EPTC | 6 | 236 | .5 | Corn | 0 | 0 | 30 MF | 45 MF |
| EPTC | 6 | 237 | .5 | Corn | 0 | 10 ST | 65 MF | 65 MF |
| EPTC | 6 | 238 | .5 | Corn | 30 ST,MF | | 75 MF | |
| EPTC | 6 | 239 | .5 | Corn | 50 ST,MF | | 80 MF | |
| EPTC | 6 | 240 | .5 | Corn | 0 | 10 MF | 25 MF | 55 MF |
| EPTC | 6 | 241 | .5 | Corn | 0 | 0 | 45 MF | 45 MF |
| EPTC | 6 | 242 | .5 | Corn | 30 ST,MF | | 50 MF | |
| EPTC | 6 | 243 | .5 | Corn | 10 ST,MF | 30 MF | 75 MF | 70 MF |
| EPTC | 6 | 244 | .5 | Corn | 0 | | 20 MF | |
| EPTC | 6 | 245 | .5 | Corn | 10 ST | | 28 MF | |
| EPTC | 6 | 246 | .5 | Corn | 0 | | 8 MF | |
| EPTC | 6 | 247 | .5 | Corn | 10 ST | | 3 MF | |
| EPTC | 6 | 248 | .5 | Corn | 20 ST | | 70 MF | |
| EPTC | 6 | 249 | .5 | Corn | 10 ST | | 70 MF | |
| EPTC | 6 | 250 | .5 | Corn | 0 | | 65 MF | |
| EPTC | 6 | 251 | .5 | Corn | 0 | | 20 MF | |
| EPTC | 6 | 252 | .5 | Corn | 0 | | 15 MF | |
| EPTC | 6 | 253 | .5 | Corn | 0 | | 8 MF | |
| EPTC | 6 | 254 | .5 | Corn | 5 MF | | 50 MF | |
| EPTC | 6 | 255 | .5 | Corn | 0 | | 5 MF | |
| EPTC | 6 | 256 | .5 | Corn | 0 | | 15 MF | |
| EPTC | 6 | 257 | .5 | Corn | 0 | | 70 MF | |
| EPTC | 6 | 258 | .5 | Corn | 0 | | 10 MF | |
| EPTC | 6 | 259 | .5 | Corn | 0 | | 35 MF | |
| EPTC | 6 | 260 | .5 | Corn | 0 | | 15 MF | |
| EPTC | 6 | 261 | .5 | Corn | 0 | | 5 MF | |
| EPTC | 6 | 262 | .5 | Corn | 0 | | 55 MF | |
| EPTC | 6 | 263 | .5 | Corn | 10 MF | | 60 MF | |
| EPTC | 6 | 264 | .5 | Corn | 0 | | 15 MF | |
| EPTC | 6 | 265 | .5 | Corn | 0 | | 70 MF | |
| EPTC | 6 | 266 | .5 | Corn | 0 | | 50 MF | |
| EPTC | 6 | 267 | .5 | Corn | 0 | | 45 MF | |
| EPTC | 6 | 268 | .5 | Corn | 0 | | 3 MF | |
| EPTC | 6 | 269 | .5 | Corn | 0 | | 35 MF | |
| EPTC | 6 | 270 | .5 | Corn | 0 | | 33 MF | |
| EPTC | 6 | 271 | .5 | Corn | 0 | | 20 MF | |
| EPTC | 6 | 272 | .5 | Corn | 0 | | 40 MF | |

TABLE III-continued

| Herbicide | Rate lb/A | Antidote Cmpd. No. | Antidote Treatment Rate % w/w | Crop | % Injury Treated Seed 2 weeks | Treated Seed 4 weeks | Untreated Seed in Adjacent Row 2 weeks | Adjacent Row 4 weeks |
|---|---|---|---|---|---|---|---|---|
| EPTC | 6 | 273 | .5 | Corn | 0 | | 45 MF | |
| EPTC | 6 | 274 | .5 | Corn | 0 | | 35 MF | |
| EPTC | 6 | 275 | .5 | Corn | 0 | | 40 MF | |
| EPTC | 6 | 276 | .5 | Corn | 0 | | 40 MF | |
| EPTC | 6 | 277 | .5 | Corn | 10 ST | | 35 MF | |
| EPTC | 6 | 278 | .5 | Corn | 0 | | 40 MF | |
| EPTC | 6 | 279 | .5 | Corn | 0 | | 33 MF | |
| EPTC | 6 | 280 | .5 | Corn | 0 | | 50 MF | |
| EPTC | 6 | 281 | .5 | Corn | 0 | | 65 MF | |
| EPTC | 6 | 282 | .5 | Corn | 10 LB | | 38 MF | |
| EPTC | 6 | 283 | .5 | Corn | 0 | | 80 MF | |
| EPTC | 6 | 284 | .5 | Corn | 0 | | 35 MF | |
| EPTC | 6 | 285 | .5 | Corn | 0 | | 75 MF | |
| EPTC | 6 | 286 | .5 | Corn | 10 ST | | 70 MF | |
| EPTC | 6 | 287 | .5 | Corn | 10 ST | | 75 MF | |
| EPTC | 6 | 288 | .5 | Corn | 10 ST | | 35 MF | |
| EPTC | 6 | 289 | .5 | Corn | 0 | | 35 MF | |
| EPTC | 6 | 290 | .5 | Corn | 0 | | 50 MF | |
| EPTC | 6 | 291 | .5 | Corn | 0 | | 50 MF | |
| EPTC | 6 | 292 | .5 | Corn | 0 | | 30 MF | |
| EPTC | 6 | 293 | .5 | Corn | 0 | | 55 MF | |
| EPTC | 6 | 294 | .5 | Corn | 0 | | 60 MF | |
| EPTC | 6 | 295 | .5 | Corn | 0 | | 25 MF | |
| EPTC | 6 | 296 | .5 | Corn | 0 | | 15 MF | |
| EPTC | 6 | 297 | .5 | Corn | 0 | | 10 MF | |
| EPTC | 6 | 298 | .5 | Corn | 0 | | 5 MF | |
| EPTC | 6 | 299 | .5 | Corn | 0 | | 20 MF | |
| EPTC | 6 | 300 | .5 | Corn | 0 | | 0 | |
| EPTC | 6 | 301 | .5 | Corn | 0 | | 23 MF | |
| EPTC | 6 | 302 | .5 | Corn | 0 | | 25 MF | |
| EPTC | 6 | 303 | .5 | Corn | 0 | | 15 MF | |
| EPTC | 6 | 304 | .5 | Corn | 0 | | 40 MF | |
| EPTC | 6 | 305 | .5 | Corn | 0 | | 35 MF | |
| EPTC | 6 | 306 | .5 | Corn | 0 | | 15 MF | |
| EPTC | 6 | 307 | .5 | Corn | 0 | | 15 MF | |
| EPTC | 6 | 308 | .5 | Corn | 0 | | 8 MF | |
| EPTC | 6 | 309 | .5 | Corn | 0 | | 25 MF | |
| EPTC | 6 | 310 | .5 | Corn | 0 | | 45 MF | |
| EPTC | 6 | 311 | .5 | Corn | 0 | | 30 MF | |
| EPTC | 6 | 312 | .5 | Corn | 0 | | 70 MF | |
| EPTC | 6 | 313 | .5 | Corn | 0 | | 65 MF | |
| EPTC | 6 | 314 | .5 | Corn | 30 ST,MF | | 60 MF | |
| EPTC | 6 | 315 | .5 | Corn | 50 MF | | 70 MF | |
| EPTC | 6 | 316 | .5 | Corn | 0 | | 0 | |
| EPTC | 6 | 317 | .5 | Corn | 0 | | 70 MF | |
| EPTC | 6 | 318 | .5 | Corn | 30 ST,MF | | 60 MF | |
| EPTC | 6 | 319 | .5 | Corn | 50 ST,MF | | 60 MF | |
| EPTC | 6 | 320 | .5 | Corn | 0 | | 0 | |
| EPTC | 6 | 321 | .5 | Corn | 0 | | 65 MF | |
| EPTC | 6 | 322 | .5 | Corn | 10 ST | | 10 MF | |
| EPTC | 6 | 323 | .5 | Corn | 10 ST | | 40 MF | |
| EPTC | 6 | 324 | .5 | Corn | 60 MF | | 75 MF | |
| EPTC | 6 | 325 | .5 | Corn | 60 MF | | 80 MF | |
| EPTC | 6 | 326 | .5 | Corn | 20 ST | | 70 MF | |
| EPTC | 6 | 327 | .5 | Corn | 30 ST,MF | | 75 MF | |
| EPTC | 6 | 328 | .5 | Corn | 60 ST,MF | | 75 MF | |
| EPTC | 6 | 329 | .5 | Corn | 0 | | 60 MF | |
| EPTC | 6 | 330 | .5 | Corn | 30 ST,MF | | 65 MF | |
| EPTC | 6 | 331 | .5 | Corn | 10 ST | | 70 MF | |
| EPTC | 6 | 332 | .5 | Corn | 0 | | 5 MF | |
| EPTC | 6 | 333 | .5 | Corn | 0 | | 15 MF | |
| EPTC | 6 | 334 | .5 | Corn | 0 | | 23 MF | |
| EPTC | 6 | 335 | .5 | Corn | 20 ST,LB | | 35 MF | |
| EPTC | 6 | 336 | .5 | Corn | 95 ST | | 30 MF | |
| EPTC | 6 | 337 | .5 | Corn | 0 | | 5 MF | |
| EPTC | 6 | 338 | .5 | Corn | 0 | | 60 MF | |
| EPTC | 6 | 339 | .5 | Corn | 30 MF | | 75 MF | |
| EPTC | 6 | 340 | .5 | Corn | 0 | | 25 MF | |
| EPTC | 6 | 341 | .5 | Corn | 0 | | 30 MF | |
| EPTC | 6 | 342 | .5 | Corn | 60 MF | | 80 MF | |
| EPTC | 6 | 343 | .5 | Corn | 0 | | 45 MF | |
| EPTC | 6 | 344 | .5 | Corn | 10 ST | | 75 MF | |
| EPTC | 6 | 345 | .5 | Corn | 0 | | 75 MF | |
| EPTC | 6 | 346 | .5 | Corn | 10 ST | | 65 MF | |
| EPTC | 6 | 347 | .5 | Corn | 50 ST,MF | | 80 MF | |
| EPTC | 6 | 348 | .5 | Corn | 0 | | 65 MF | |
| EPTC | 6 | 349 | .5 | Corn | 60 ST,MF | | 75 MF | |

TABLE III-continued

| | | Antidote | | | % Injury | | | |
|---|---|---|---|---|---|---|---|---|
| | | | | | Treated Seed | | Untreated Seed in Adjacent Row | |
| Herbicide | Rate lb/A | Cmpd. No. | Treatment Rate % w/w | Crop | 2 weeks | 4 weeks | 2 weeks | 4 weeks |
| EPTC | 6 | 350 | .5 | Corn | 60 MF | | 80 MF | |
| EPTC | 6 | 351 | .5 | Corn | 60 ST,MF | | 75 MF | |
| EPTC | 6 | 352 | .5 | Corn | 60 ST,MF | | 80 MF | |
| EPTC | 6 | 353 | .5 | Corn | 60 ST,MF | | 75 MF | |
| EPTC | 6 | 354 | .5 | Corn | 50 ST,MF | | 80 MF | |
| EPTC | 6 | 355 | .5 | Corn | 60 ST,MF | | 70 MF | |
| EPTC | 6 | 356 | .5 | Corn | 50 ST,LB | | 70 MF | |
| EPTC | 6 | 357 | .5 | Corn | 60 MF | | 80 MF | |
| EPTC | 6 | 358 | .5 | Corn | 30 ST | | 75 MF | |
| EPTC | 6 | 359 | .5 | Corn | 30 ST,MF | | 75 MF | |
| EPTC | 6 | 360 | .5 | Corn | 50 ST,MF | | 70 MF | |
| EPTC | 6 | 361 | .5 | Corn | 50 ST,MF | | 75 MF | |
| EPTC | 6 | 362 | .5 | Corn | 30 ST | | 75 MF | |
| EPTC | 6 | 363 | .5 | Corn | 30 ST,MF | | 80 MF | |
| EPTC | 6 | 364 | .5 | Corn | 10 ST | | 55 MF | |
| EPTC | 6 | 365 | .5 | Corn | 50 ST,MF | | 65 MF | |
| EPTC | 6 | 366 | .5 | Corn | 0 | | 65 MF | |
| EPTC | 6 | 367 | .5 | Corn | 0 | | 75 MF | |
| EPTC | 6 | 368 | .5 | Corn | 0 | | 30 MF | |
| EPTC | 6 | 369 | .5 | Corn | 0 | | 25 MF | |
| EPTC | 6 | 370 | .5 | Corn | 70 LB | 70 MF | 80 MF | 80 MF |
| EPTC | 6 | 371 | .5 | Corn | 40 ST | 50 MF | 85 MF | 80 MF |
| EPTC | 6 | 372 | .5 | Corn | 30 ST | 40 ST,MF | 80 MF | 80 MF |
| EPTC | 6 | 373 | .5 | Corn | 30 ST,MF,LB | | 75 MF | |
| EPTC | 6 | 374 | .5 | Corn | 60 MF | | 85 MF | |
| EPTC | 6 | 375 | .5 | Corn | 50 ST,LB | 30 MF | 90 MF | 80 MF |
| EPTC | 6 | 376 | .5 | Corn | 50 MF | | 90 MF | |
| EPTC | 6 | 377 | .5 | Corn | 40 ST,MF | | 70 MF | |
| EPTC | 6 | 378 | .5 | Corn | 80 MF | | | |
| EPTC | 6 | 379 | .5 | Corn | 50 MF | | 85 MF | |
| EPTC | 6 | 380 | .5 | Corn | 10 ST | 20 MF | 90 MF | 80 MF |
| EPTC | 6 | 381 | .5 | Corn | 30 ST | 40 MF | 85 MF | 80 MF |
| EPTC | 6 | 382 | .5 | Corn | 50 MF | | 80 MF | |
| EPTC | 6 | 383 | .5 | Corn | 50 ST,LB | 30 ST | 90 MF | 80 MF |
| EPTC | 6 | 384 | .5 | Corn | 20 ST | 10 ST | 70 MF | 80 MF |
| EPTC | 6 | 385 | .5 | Corn | 60 MF | | 85 MF | |
| EPTC | 6 | 386 | .5 | Corn | 10 ST | 30 MF | 75 MF | |
| EPTC | 6 | 387 | .5 | Corn | 60 MF | | 80 MF | |
| EPTC | 6 | 388 | .5 | Corn | 100 IG | | 55 MF | |
| EPTC | 6 | 389 | .5 | Corn | 10 ST | 0 | 75 MF | |
| EPTC | 6 | 390 | .5 | Corn | 15 ST,MF | | 80 MF | |
| EPTC | 6 | 391 | .5 | Corn | 10 ST | 0 | 80 MF | |
| EPTC | 6 | 392 | .5 | Corn | 60 ST,MF | | 75 MF | |
| EPTC | 6 | 393 | .5 | Corn | 60 MF | | 80 MF | |
| EPTC | 6 | 394 | .5 | Corn | 50 ST,MF | | 80 MF | |
| EPTC | 6 | 395 | .5 | Corn | 10 ST | 10 MF | 65 MF | |
| EPTC | 6 | 396 | .5 | Corn | 10 ST | 0 | 75 MF | |
| EPTC | 6 | 397 | .5 | Corn | 10 ST | 20 MF | 60 MF | |
| EPTC | 6 | 398 | .5 | Corn | 60 MF | | 80 MF | |
| EPTC | 6 | 399 | .5 | Corn | 60 MF | | 80 MF | |
| EPTC | 6 | 400 | .5 | Corn | 60 MF | | 75 MF | |
| EPTC | 6 | 401 | .5 | Corn | 60 MF | | 80 MF | |
| EPTC | 6 | 402 | .5 | Corn | 40 ST,MF | | 75 MF | |
| EPTC | 6 | 403 | .5 | Corn | 60 ST,MF | | 80 MF | |
| EPTC | 6 | 404 | .5 | Corn | 70 MF | | 80 MF | |
| EPTC | 6 | 405 | .5 | Corn | 70 MF | | 80 MF | |
| EPTC | 6 | 406 | .5 | Corn | 70 MF | | 80 MF | |
| EPTC | 6 | 407 | .5 | Corn | 70 MF | | 80 MF | |
| EPTC | 6 | 408 | .5 | Corn | 70 MF | | 80 MF | |
| EPTC | 6 | 409 | .5 | Corn | 70 MF | | 80 MF | |
| EPTC | 6 | 410 | .5 | Corn | 70 MF | | 80 MF | |
| EPTC | 6 | 411 | .5 | Corn | 60 MF | | 80 MF | |
| EPTC | 6 | 412 | .5 | Corn | 70 MF | | 80 MF | |
| EPTC | 6 | 413 | .5 | Corn | 70 MF | | 80 MF | |
| EPTC | 6 | 414 | .5 | Corn | 70 MF | | 80 MF | |
| EPTC | 6 | 415 | .5 | Corn | 70 MF | | 80 MF | |
| EPTC | 6 | 416 | .5 | Corn | 70 MF | | 80 MF | |
| EPTC | 6 | 417 | .5 | Corn | 60 MF | | 80 MF | |
| EPTC | 6 | 418 | .5 | Corn | 70 MF | | 80 MF | |
| EPTC | 6 | 419 | .5 | Corn | 70 MF | | 80 MF | |
| EPTC | 6 | 420 | .5 | Corn | 70 MF | | 80 MF | |
| EPTC | 6 | 421 | .5 | Corn | 70 MF | | 80 MF | |
| EPTC | 6 | 422 | .5 | Corn | 70 MF | | 80 MF | |
| EPTC | 6 | 423 | .5 | Corn | 70 MF | | 80 MF | |
| EPTC | 6 | 424 | .5 | Corn | 70 MF | | 80 MF | |
| EPTC | 6 | 425 | .5 | Corn | 70 MF | | 80 MF | |

TABLE III-continued

| Herbicide | Rate lb/A | Antidote Cmpd. No. | Treatment Rate % w/w | Crop | % Injury Treated Seed 2 weeks | 4 weeks | Untreated Seed in Adjacent Row 2 weeks | 4 weeks |
|---|---|---|---|---|---|---|---|---|
| EPTC | 6 | 426 | .5 | Corn | 60 ST,MF | | 75 MF | |
| EPTC | 6 | 427 | .5 | Corn | 70 MF | | 75 MF | |
| EPTC | 6 | 428 | .5 | Corn | 70 MF | | 75 MF | |
| EPTC | 6 | 429 | .5 | Corn | 70 ST,MF | | 80 MF | |
| EPTC | 6 | 430 | .5 | Corn | 70 ST,MF | | 75 MF | |
| EPTC | 6 | 431 | .5 | Corn | 70 ST,MF | | 80 MF | |
| EPTC | 6 | 432 | .5 | Corn | 70 ST,MF | | 80 MF | |
| EPTC | 6 | 433 | .5 | Corn | 70 MF | | 80 MF | |
| EPTC | 6 | 434 | .5 | Corn | 70 ST,MF | | 80 MF | |
| EPTC | 6 | 435 | .5 | Corn | 70 MF | | 75 MF | |
| EPTC | 6 | 436 | .5 | Corn | 60 ST,MF | | 75 MF | |
| EPTC | 6 | 437 | .5 | Corn | 50 ST,MF | | 75 MF | |
| EPTC | 6 | 438 | .5 | Corn | 70 ST,MF | | 80 MF | |
| EPTC | 6 | 439 | .5 | Corn | 20 ST | | 75 MF | |
| EPTC | 6 | 440 | .5 | Corn | 10 ST | | 65 MF | |
| EPTC | 6 | 441 | .5 | Corn | 30 ST | | 75 MF | |
| EPTC | 6 | 442 | .5 | Corn | 10 ST | | 70 MF | |
| EPTC | 6 | 443 | .5 | Corn | 10 ST | | 80 MF | |
| EPTC | 6 | 444 | .5 | Corn | 10 ST | | 65 MF | |
| EPTC | 6 | 445 | .5 | Corn | 70 MF | | 75 MF | |
| EPTC | 6 | 446 | .5 | Corn | 20 ST | | 65 MF | |
| EPTC | 6 | 447 | .5 | Corn | 60 MF | | 80 MF | |
| EPTC | 6 | 448 | .5 | Corn | 30 ST,MF | | 70 MF | |
| EPTC | 6 | 449 | .5 | Corn | 70 MF | | 80 MF | |
| EPTC | 6 | 450 | .5 | Corn | 60 ST,MF | | 80 MF | |
| EPTC | 6 | 451 | .5 | Corn | 20 ST | | 70 MF | |
| EPTC | 6 | 452 | .5 | Corn | 70 ST,MF | | 80 MF | |
| EPTC | 6 | 453 | .5 | Corn | 20 ST | | 60 MF | |
| EPTC | 6 | 454 | .5 | Corn | 70 MF | | 75 MF | |
| EPTC | 6 | 455 | .5 | Corn | 20 ST | | 65 MF | |
| EPTC | 6 | 456 | .5 | Corn | 60 ST,MF | | 75 MF | |
| EPTC | 6 | 457 | .5 | Corn | 70 ST,MF | | 80 MF | |
| EPTC | 6 | 458 | .5 | Corn | 50 ST,MF | | 70 MF | |
| EPTC | 6 | 459 | .5 | Corn | 40 ST,MF | | 80 MF | |
| EPTC | 6 | 460 | .5 | Corn | 60 ST,MF | | 80 MF | |
| EPTC | 6 | 461 | .5 | Corn | 10 ST | | 80 MF | |
| EPTC | 6 | 462 | .5 | Corn | 30 ST,MF | | 75 MF | |
| EPTC | 6 | 463 | .5 | Corn | 70 MF | | 80 MF | |
| EPTC | 6 | 464 | .5 | Corn | 70 MF | | 80 MF | |
| EPTC | 6 | 465 | .5 | Corn | 50 ST,MF | | 80 MF | |
| EPTC | 6 | 466 | .5 | Corn | 20 ST,MF | | 70 MF | |
| EPTC | 6 | 467 | .5 | Corn | 0 | | 75 MF | |
| EPTC | 6 | 468 | .5 | Corn | 60 ST,MF | | 80 MF | |
| EPTC | 6 | 469 | .5 | Corn | 10 ST | | 80 MF | |
| EPTC | 6 | 470 | .5 | Corn | 60 MF | | 75 MF | |
| EPTC | 6 | 471 | .5 | Corn | 50 ST,MF | | 65 MF | |
| EPTC | 6 | 472 | .5 | Corn | 20 ST,MF | | 25 MF | |
| EPTC | 6 | 473 | .5 | Corn | 70 MF | | 80 MF | |
| EPTC | 6 | 474 | .5 | Corn | 70 MF | | 80 MF | |
| EPTC | 6 | 475 | .5 | Corn | 20 ST,MF | | 70 MF | |
| EPTC | 6 | 476 | .5 | Corn | 10 ST | | 75 MF | |
| EPTC | 6 | 477 | .5 | Corn | 30 ST,MF | | 80 MF | |
| EPTC | 6 | 478 | .5 | Corn | 20 ST,MF | | 80 MF | |
| EPTC | 6 | 479 | .5 | Corn | 60 ST,MF | | 80 MF | |
| EPTC | 6 | 480 | .5 | Corn | 70 ST,MF | | 80 MF | |
| EPTC | 6 | 481 | .5 | Corn | 70 MF | | 80 MF | |
| EPTC | 6 | 482 | .5 | Corn | 60 ST,MF | | 80 MF | |
| EPTC | 6 | 483 | .5 | Corn | 70 ST,MF | | 80 MF | |
| EPTC | 6 | 484 | .5 | Corn | 60 MF | | 75 MF | |
| EPTC | 6 | 485 | .5 | Corn | 70 MF | | 80 MF | |
| EPTC | 6 | 486 | .5 | Corn | 10 ST | | 25 MF | |
| EPTC | 6 | 487 | .5 | Corn | 10 ST | | 40 MF | |
| EPTC | 6 | 488 | .5 | Corn | 50 ST,MF | | 55 MF | |
| EPTC | 6 | 489 | .5 | Corn | 0 | | 0 | |
| EPTC | 6 | 490 | .5 | Corn | 10 ST | 30 ST | 70 | 70 MF |
| EPTC | 6 | 491 | .5 | Corn | 20 | 50 ST,MF | 70 | 70 MF |
| EPTC | 6 | 492 | .5 | Corn | 50 | 75 ST,MF | 80 MF | |
| EPTC | 6 | 493 | .5 | Corn | 40 ST,MF | | 80 ST,MF | |
| EPTC | 6 | 494 | .5 | Corn | 0 | 50 ST,MF | 75 MF | 85 MF |
| EPTC | 6 | 495 | .5 | Corn | 10 ST | 0 | 77 MF | 75 MF |
| EPTC | 6 | 496 | .5 | Corn | 30 ST,MF | 60 ST,MF | 95 MF | 98 MF |
| EPTC | 6 | 497 | .5 | Corn | 50 MF | | 98 MF | |
| EPTC | 6 | 498 | .5 | Corn | 30 ST,MF | | 97 MF | |
| EPTC | 6 | 499 | .5 | Corn | 60 MF | | 98 MF | |
| EPTC | 6 | 500 | .5 | Corn | 10 ST | 20 ST | 78 MF | 97 MF |
| EPTC | 6 | 501 | .5 | Corn | 10 ST | 20 ST | 50 MF | 70 |
| EPTC | 6 | 502 | .5 | Corn | 100 IG | 100 IG | 55 MF | 60 MF |

TABLE III-continued

| | | Antidote | | | % Injury | | | |
|---|---|---|---|---|---|---|---|---|
| | Rate | Cmpd. | Treatment Rate | | Treated Seed | | Untreated Seed in Adjacent Row | |
| Herbicide | lb/A | No. | % w/w | Crop | 2 weeks | 4 weeks | 2 weeks | 4 weeks |
| EPTC | 6 | 503 | .5 | Corn | 100 IG | 100 IG | 30 MF | 40 MF |
| EPTC | 6 | 504 | .5 | Corn | 0 | 0 | 5 MF | 30 MF |
| EPTC | 6 | 505 | .5 | Corn | 30 ST | 30 ST | 0 | 0 |
| EPTC | 6 | 506 | .5 | Corn | 10 ST | 25 MF | 58 MF | |
| EPTC | 6 | 507 | .5 | Corn | 20 ST,MF | | 65 MF | |
| EPTC | 6 | 508 | .5 | Corn | 10 ST | | 78 MF | |
| EPTC | 6 | 509 | .5 | Corn | 40 ST,MF | | 89 MF | |
| EPTC | 6 | 510 | .5 | Corn | 0 | 0 | 84 MF | 94 |
| EPTC | 6 | 511 | .5 | Corn | 100 IG | 100 IG | 45 MF | 50 MF |
| EPTC | 6 | 512 | .5 | Corn | 100 IG | 100 IG | 0 | 0 |
| EPTC | 6 | 513 | .5 | Corn | 100 IG | 100 IG | 0 | 0 |
| EPTC | 6 | — | — | Corn | 90 MF | | | |
| S—2,3,3-Trichloroallyl diisopropyl thiolcarbamate | 1 | 6 | .25 | Wheat | 5 ST | | | |
| S—2,3,3-Trichloroallyl diisopropyl thiolcarbamate | 1 | 6 | .5 | Wheat | 20 ST | | | |
| S—2,3,3-Trichloroallyl diisopropyl thiolcarbamate | 1 | — | — | Wheat | 90 MF | | | |
| EPTC + 2-chloro-4-ethylamino-6-isopropylamino-s-triazine | 6 + 1 | 6 | 1.0 | Corn | 0 | 0 | 0 | 0 |
| EPTC + 2-chloro-4-ethylamino-6-isopropylamino-s-triazine | 6 + 1 | 6 | 0.01 | Corn | 0 | 0 | | |
| EPTC + 2-chloro-4,6-bis(ethylamino)-s-triazine | 6 + 1 | 6 | 1.0 | Corn | 0 | 0 | 0 | 0 |
| EPTC + 2-chloro-4,6-bis(ethylamino)-s-triazine | 6 + 1 | 6 | 0.01 | Corn | 0 | 0 | | |
| EPTC + 2(4-chloro-6-ethylamino-s-triazine-2-yl-amino)-2-methylpropionitrile | 6 + 1 | 6 | 1.0 | Corn | 0 | 0 | 0 | 0 |
| EPTC + 2(4-chloro-6-ethylamino-s-triazine-2-yl-amino)-2-methylpropionitrile | 6 + 1 | 6 | 0.01 | Corn | 0 | 0 | | |
| EPTC + 2-chloro-4-cyclopropylamino-6-isopropylamino-s-triazine | 6 + 1 | 6 | 1.0 | Corn | 0 | 0 | 0 | 0 |
| EPTC + 2-chloro-4-cyclopropylamino-6-isopropylamino-s-triazine | 6 + 1 | 6 | 0.01 | Corn | 0 | 0 | | |
| EPTC + 2,4-D | 6 + 1 | 6 | 1.0 | Corn | 0 | 0 | 0 | 0 |
| EPTC + 2,4-D | 6 + 1 | 6 | 0.01 | Corn | 0 | 0 | | |
| S—propyl dipropyl thiolcarbamate + 2-chloro-4-ethylamino-6- | 6 + 1 | 6 | 1.0 | Corn | 0 | 0 | 0 | 0 |

TABLE III-continued

| Herbicide | Rate lb/A | Antidote Cmpd. No. | Antidote Treatment Rate % w/w | Crop | % Injury Treated Seed 2 weeks | % Injury Treated Seed 4 weeks | % Injury Untreated Seed in Adjacent Row 2 weeks | % Injury Untreated Seed in Adjacent Row 4 weeks |
|---|---|---|---|---|---|---|---|---|
| isopropylamino-s-triazine | | | | | | | | |
| S—propyl dipropyl thiolcarbamate | 6 | — | — | Corn | 90 MF | | | |
| S—propyl dipropyl thiolcarbamate + 2-chloro-4-ethylamino-6-isopropylamino-s-triazine | 6 + 1 | 6 | 0.01 | Corn | 0 | 0 | 0 | 0 |
| S—propyl dipropyl thiolcarbamate + 2-chloro-4,6-bis(ethylamino)-s-triazine | 6 + 1 | 6 | 1.0 | Corn | 0 | 0 | 0 | 0 |
| S—propyl dipropyl thiolcarbamate + 2-chloro-4,6-bis(ethylamino)-s-triazine | 6 + 1 | 6 | 0.01 | Corn | 0 | 0 | 0 | 0 |
| S—propyl dipropyl thiolcarbamate + 2(4-chloro-6-ethylamino-s-triazine-2-yl-amino)-2-methyl-propionitrile | 6 + 1 | 6 | 1.0 | Corn | 0 | 0 | 0 | 0 |
| S—propyl dipropyl thiolcarbamate + 2(4-chloro-6-ethylamino-s-triazine-2-yl-amino)-2-methyl-propionitrile | 6 + 1 | 6 | 0.01 | Corn | 0 | 0 | | |
| S—propyl dipropy thiolcarbamate + 2-chloro-4-cyclopropyl-amino-6-iso-propylamino-s-triazine | 6 + 1 | 6 | 1.0 | Corn | 0 | 0 | 0 | 0 |
| S—propyl dipropyl thiolcarbamate + 2-chloro-4-cyclopropyl-amino-6-iso-propylamino-s-triazine | 6 + 1 | 6 | 0.01 | Corn | 0 | 0 | | |
| S—propyl dipropyl thiolcarbamate + 2,4-D | 6 + 1 | 6 | 1.0 | Corn | 0 | 0 | 0 | 0 |
| S—propyl dipropyl thiolcarbamate + 2,4-D | 6 + 1 | 6 | 0.01 | Corn | 0 | 0 | | |
| S—propyl dipropyl thiolcarbamate | 6 | 6 | 1.0 | Corn | 0 | 0 | 0 | 0 |
| S—propyl dipropyl thiolcarbamate | 6 | 6 | 0.01 | Corn | 0 | 0 | | |
| S—ethyl diisobutyl thiolcarbamate + 2-chloro-4-ethylamino-6-isopropylamino-s-triazine | 8 + 1 | 6 | 1.0 | Corn | 0 | 0 | 0 | 0 |

TABLE III-continued

| Herbicide | Rate lb/A | Antidote Cmpd. No. | Antidote Treatment Rate % w/w | Crop | % Injury Treated Seed 2 weeks | % Injury Treated Seed 4 weeks | Untreated Seed in Adjacent Row 2 weeks | Untreated Seed in Adjacent Row 4 weeks |
|---|---|---|---|---|---|---|---|---|
| S—ethyl diisobutyl thiolcarbamate + 2-chloro-4-ethylamino-6-isopropylamino-s-triazine | 8 + 1 | 6 | 0.01 | Corn | 0 | 0 | | |
| S—ethyl diisobutyl thiolcarbamate + 2-chloro-4,6-bis(ethylamino)-s-triazine | 8 + 1 | 6 | 1.0 | Corn | 0 | 0 | 0 | 0 |
| S—ethyl diisobutyl thiolcarbamate + 2-chloro-4,6-bis(ethylamino)-s-triazine | 8 + 1 | 6 | 0.01 | Corn | 0 | 0 | | |
| S—ethyl diisobutyl thiolcarbamate + 2(4-chloro-6-ethylamino-s-triazine-2-yl-amino)-2-methyl-propionitrile | 8 + 1 | 6 | 1.0 | Corn | 0 | 0 | 0 | 0 |
| S—ethyl diisobutyl thiolcarbamate + 2(4-chloro-6-ethylamino-s-triazine-2-yl-amino)-2-methyl-propionitrile | 8 + 1 | 6 | 0.01 | Corn | 0 | 0 | | |
| S—ethyl diisobutyl thiolcarbamate + 2-chloro-4-cyclopropyl-amino-6-iso-propylamino-s-triazine | 8 + 1 | 6 | 1.0 | Corn | 0 | 0 | 0 | 0 |
| S—ethyl diisobutyl thiolcarbamate + 2-chloro-4-cyclopropyl-amino-6-iso-propylamino-s-triazine | 8 + 1 | 6 | 0.01 | Corn | 0 | 0 | | |
| S—ethyl diisobutyl thiolcarbamate + 2,4-D | 8 + 1 | 6 | 1.0 | Corn | 0 | 0 | 0 | 0 |
| S—ethyl diisobutyl thiolcarbamate + 2,4-D | 8 + 1 | 6 | 0.01 | Corn | 0 | 0 | | |
| S—ethyl diisobutyl thiolcarbamate | 8 | 6 | 1.0 | Corn | 0 | 0 | 0 | 0 |
| S—ethyl diisobutyl thiolcarbamate | 8 | 6 | 0.01 | Corn | 0 | 0 | 0 | 0 |
| S—2,3,3-tri-chloroallyl-diisopropyl thiolcarbamate | 8 | 6 | 1.0 | Corn | 0 | 0 | 0 | 0 |
| S—2,3,3-tri-chloroallyl-diisopropyl thiolcarbamate | 8 | 6 | 0.01 | Corn | 0 | 0 | 0 | 0 |
| S—ethyl diisobutyl thiolcarbamate | 8 | — | — | Corn | 20 MF | | | |
| S—2,3,3-tri- | 8 | — | — | Corn | 30 ST | | | |

TABLE III-continued

| Herbicide | Rate lb/A | Antidote Cmpd. No. | Treatment Rate % w/w | Crop | % Injury Treated Seed 2 weeks | 4 weeks | Untreated Seed in Adjacent Row 2 weeks | 4 weeks |
|---|---|---|---|---|---|---|---|---|
| chloroallyl-diisopropyl thiolcarbamate | | | | | | | | |

EPTC = S—ethyl, dipropylthiocarbamate
ST = stunting
MF = malformation
IG = inhibited germination
LB = leaf burn The antidote compounds of the present invention can be used in any convenient form. Thus, the antidote compounds can be made into emulsifiable liquids, emulsifiable concentrates, liquid, wettable powder, powders, granular or any other convenient form. In its preferred form, the antidote compounds are admixed with the thiolcarbamates and incorporated into the soil prior to or after planting the seed. It is to be understood, however, that the thiolcarbamate herbicide can be incorporated into the soil and thereafter the antidote compound can be incorporated into the soil. Moreover, the seed can be treated with the antidote compound and planted into the soil which has been treated with herbicides or untreated with the herbicide and subsequently treated with the herbicide. The method of addition of the antidote compound does not affect the herbicidal activity of the carbamate compounds.

The amount of antidote composition present can range between about 0.0001 to about 30 parts by weight per each part by weight of thiolcarbamate herbicide. The exact amount of antidote compound will usually be determined on economic ratios for the most effective amount usable.

When used in the claims of this application, the phrase "active herbicidal compound" is meant to include the active thiolcarbamates alone or the thiolcarbamates admixed with other active compounds such as the s-triazines and 2,4-D, or the active acetanilides and the like. Also, the active herbicidal compound is different from the antidote compound.

It is clear that the classes of herbicidal agents described and illustrated herein are characterized as effective herbicides exhibiting such activity. The degree of this herbicidal activity varies among specific compounds and among combinations of specific compounds within the classes. Similarly, the degree of activity to some exttent varies among the species of plants to which a specific herbicidal compound or combination may be applied. Thus, selection of a specific herbicidal compound or combination to control undesirable plant species readily may be made. Within the present invention the prevention of injury to a desired crop species in the presence of a specific compound or combination may be achieved. The beneficial plant species which can be protected by this method is not intended to be limited by the specific crops employed in the examples.

The herbicidal compounds employed in the method of this invention are active herbicides of a general type. That is, the members of the classes are herbicidally effectivve against a wide range of plant species with no discrimination between desirable and undesirable species. The method of controlling vegetation comprises applying an herbicidally effective amount of the herein-described herbicidal compounds to the area or plant locus where control is desired.

An herbicide as used herein means a compound which controls or modifies the growth of vegetation or plants. Such controlling or modifying effects include all deviations from natural development; for example, killing, retardation, defoliation, desiccation, regulation, stunting, tillering, stimulation, dwarfing and the like. By "plants" it is meant germinant seeds, emerging seedlings, and established vegetation, including the roots and above-ground portions.

The herbicides in the tables are used at rates which produce effective control of undesirable vegetation. The rates are within the recommended amounts set forth by the supplier. Therefore, the weed control in each instance is commercially acceptable within the desired amount.

In the above description of the antidote compounds, the following embodiments are intended for the various substituent groups: alkyl includes, unless otherwise provided for, those members which contain form 1 to 20 carbon atoms, inclusive, in both straight and branched chain configurations; alkenyl includes, unless otherwise provided for, those members which coontain at least one olefinic double bond and contain from 2 to 20 carbon atoms, inclusive, preferably from 2 to 12 carbon atoms, inclusive, in both straight and branched chain configurations; and alkynyl includes, unless otherwise provided for, those members which contain at least one acetylenic triple bond and contain from 2to 20 carbon atoms, inclusive, preferably from 2 to 12 carbon atoms, inclusive, in both straight and branched chain configurations.

What is claimed is:

1. A herbicide composition comprising an active thiolcarbamate herbicide and a non-phytotoxic, antidotally effective amount of an amide of dichloroacetic acid, said amide of dichloroacetic acid being antidotally active with said thiolcarbamate herbicide, provided that said amide is other than a N,N-dihydro or a N-hydro, N-halophenyl amide of dichloroacetic acid.

2. The herbicide composition according to claim 1 wherein said amid of dichloroacetic acid is a ($C_2$–$C_{12}$alkenyl) amide of dichloroaceticacid.

3. The herbicide composition according to claim 2 wherein said ($C_2$–$C_{12}$alkenyl) amide of dichloroacetic acid is an allyl amide of dichloroacetic acid.

4. The herbicide composition according to claim 3 wherein said allyl amide of dichloroacetic acid is a N-allyl, N-($C_3$–$C_4$ alkyl) amide of dichloroacetic acid.

5. The composition as set forth in claim 4 wherein said alkyl is i-$C_3H_7$.

6. The composition as set forth in claim 4 wherein said alkyl is n-$C_3H_7$.

7. The composition as set forth in claim 4 wherein said alkyl is n-$C_4H_9$.

8. The composition as set forth in claim 4 wherein said alkyl is i-$C_4H_9$.

* * * * *

UNITED STATES PATENT AND TRADEMARK OFFICE
CERTIFICATE OF CORRECTION

PATENT NO. : 4,415,353

DATED : November 15, 1983

INVENTOR(S) : Ferenc M. Pallos, Mervin E. Brokke, Duane R. Arneklev

It is certified that error appears in the above-identified patent and that said Letters Patent is hereby corrected as shown below:

In Column 2, at line 3, ..."pheylcycloalkyl;..." should read phenylcycloalkyl

In Column 2, at line 68, ...$n_C^{30}$ should read $n_D^{30}$

In column 6, formula under Example 15 should read

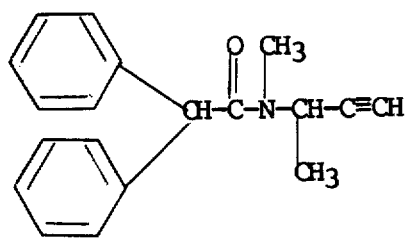

In column 22, compound 75, formula under column $R_1$ should read  $-CH_3$

In column 22, compound 75, formula under column $R_2$ should read $-CH(CH_3)-C\equiv CH$ In column 39, compound 175, under column R, formula under ring should read O=C-OH In column 48, compound 243, formula under R column should read

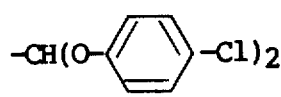

In Columns 53, 54, 55, and 56, compound nos. 269 through and including 280, rings for formulas should be open left side.

UNITED STATES PATENT AND TRADEMARK OFFICE
CERTIFICATE OF CORRECTION

PATENT NO. : 4,415,353

DATED : November 15, 1983

INVENTOR(S) : Ferenc M. Pallos, Mervin E. Brokke, Duane R. Arneklev

It is certified that error appears in the above-identified patent and that said Letters Patent is hereby corrected as shown below:

In Column 58, formula 286, bottom ring of compound should be open left side.

In Column 59, formula 287, bottom ring of compound should be open left side.

In column 61, compound 296, formula under column $R_1$ should be

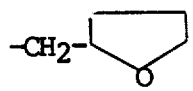

In column 62, compounds 305, 306, 307, rings for formulas should be open left side.

In column 63, compound 308, ring for formula should be open left side.

In column 64, compounds 317 and 320, rings for formulas should be open left side.

In column 64, compound 322, formula under column $R_2$ should read

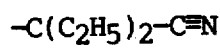

In column 68, compounds 336 and 337, formulas under column $R_2$ should read

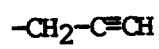

In column 68, compound 341, formula under $R_2$ column should read

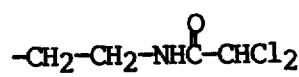

UNITED STATES PATENT AND TRADEMARK OFFICE
CERTIFICATE OF CORRECTION

PATENT NO. : 4,415,353

DATED : November 15, 1983

INVENTOR(S) : Ferenc M. Pallos, Mervin E. Brokke, Duane R. Arneklev

It is certified that error appears in the above-identified patent and that said Letters Patent is hereby corrected as shown below:

In column 74, compound 363, formula under $R_2$ column should read $$-C(CH_3)_2-C\equiv CH$$

In columns 75 and 76, compound 367, formula under column $R_1$ column should be moved to the right to be between columns $R_1$ and $R_2$, and bottom ring should be open on left side.

In column 79, compound 382, formula under $R_2$ column should read $$-C(CH_3)_2-C\equiv CH$$

In column 80, compound 386, ring should be open left side.

In column 83, compound 398, formula under R column should read $$-CH_2-O-C(CHCl_2)(CCl_3)-OH$$

In column 88, compound 413, bottom ring of formula should be open left side.

In column 88, compounds 414 and 415, rings should be open left side.

UNITED STATES PATENT AND TRADEMARK OFFICE
CERTIFICATE OF CORRECTION

PATENT NO. : 4,415,353

DATED : November 15, 1983

INVENTOR(S) : Ferenc M. Pallos, Mervin E. Brokke, Duane R. Arneklev

It is certified that error appears in the above-identified patent and that said Letters Patent is hereby corrected as shown below:

In column 101, compound 489, ring should be open left side.

In column 102, compounds 495 and 497, rings for formulas should be open left side.

In column 103, compounds 498 and 499, rings for formulas should be open left side.

In column 104, compound 510, formula on bottom left side of ring should read $C_2H_5$ In column 134, line 23, "The herbicides in..." should read "The herbicides indicated ..."

Signed and Sealed this

Eleventh Day of February 1986

[SEAL]

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,415,353
DATED : November 15, 1983
INVENTOR(S) : Ferenc M. Pallos et al.

It is certified that error appears in the above-identified patent and that said Letters Patent is hereby corrected as shown below:

In Column 123, Table III-continued, entries under 4th column "Treatment Rate % w/w", should read .05 for Compound numbers 404 through 425.

In Column 125, Table III-continued, entries under 4th column "Treatment Rate % w/w", should read .05 for Compound numbers 426 through 489.

Signed and Sealed this

Thirtieth Day of December, 1986

Attest:

DONALD J. QUIGG

*Attesting Officer*   *Commissioner of Patents and Trademarks*